(12) United States Patent
Dubois et al.

(10) Patent No.: US 7,745,467 B2
(45) Date of Patent: *Jun. 29, 2010

(54) N-(HETEROARYL)-1-HETEROARYLALKYL-1 H-INDOLE-2-CARBOXAMIDE DERIVATIVES, PREPARATION AND THERAPEUTIC USE THEREOF

(75) Inventors: Laurent Dubois, Le Plessis-Robinson (FR); Yannick Evanno, Dannemois (FR); Andre Malanda, Villejust (FR)

(73) Assignee: Sanofi-Aventis, Paris (FR)

( * ) Notice: Subject to any disclaimer, the term of this patent is extended or adjusted under 35 U.S.C. 154(b) by 106 days.

This patent is subject to a terminal disclaimer.

(21) Appl. No.: 11/970,878

(22) Filed: Jan. 8, 2008

(65) Prior Publication Data

US 2008/0146646 A1 Jun. 19, 2008

Related U.S. Application Data

(63) Continuation of application No. PCT/FR2006/001782, filed on Jul. 20, 2006.

(30) Foreign Application Priority Data

Jul. 22, 2005 (FR) .................................. 05 07803

(51) Int. Cl.
*A61K 31/44* (2006.01)
*C07D 401/06* (2006.01)
(52) U.S. Cl. ................. 514/339; 546/268.1; 546/268.4; 546/272.7; 546/273.4; 514/336; 514/337
(58) Field of Classification Search .............. 546/268.1, 546/268.4, 272.7, 273.4; 514/336, 337, 339
See application file for complete search history.

(56) References Cited

U.S. PATENT DOCUMENTS 6,906,084 B2 * 6/2005 Nazare et al. ............... 514/323

| | | | | |
|---|---|---|---|---|
| 7,196,103 | B2 * | 3/2007 | Nazare et al. ................ | 514/340 |
| 7,384,969 | B2 * | 6/2008 | Dubois et al. ................ | 514/414 |
| 7,407,950 | B2 * | 8/2008 | Dubois et al. ........... | 514/211.09 |
| 7,557,134 | B2 * | 7/2009 | Dubois et al. ................ | 514/414 |
| 7,582,671 | B2 * | 9/2009 | Dubois et al. ................ | 514/414 |

FOREIGN PATENT DOCUMENTS

| | | |
|---|---|---|
| EP | 1314733 | 5/2003 |
| WO | WO 01/32622 | 5/2001 |
| WO | WO 03/028719 | 4/2003 |
| WO | WO 03/068749 | 8/2003 |
| WO | WO 2004/056768 | 7/2004 |
| WO | WO 2004/072069 | 8/2004 |
| WO | WO 2006/072736 | 7/2006 |
| WO | WO 2007/010138 | 1/2007 |

OTHER PUBLICATIONS

Brands, M., et. al., Novel, Selective indole-Based ECE Inhibitors: Lead Optimization Via Solid-Phase and Classical Synthesis, Bioorganic & Medicinal Chemistry Letters, vol. 15, (2005), pp. 4201-4205.

* cited by examiner

*Primary Examiner*—Golam M Shameem
(74) *Attorney, Agent, or Firm*—Balaram Gupta

(57) ABSTRACT

The invention concerns compounds of general formula (I), wherein n, $X_1$, $X_2$, $X_3$, $X_4$, Y and W are as defined herein.

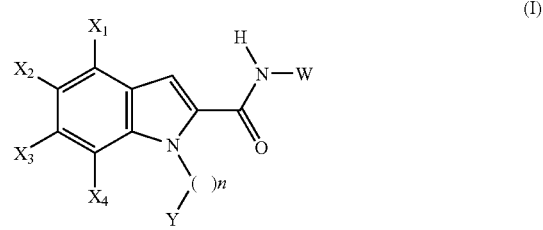

The invention also concerns a method for preparing said compounds and their therapeutic use.

15 Claims, No Drawings

N-(HETEROARYL)-1-HETEROARYLALKYL-1H-INDOLE-2-CARBOXAMIDE DERIVATIVES, PREPARATION AND THERAPEUTIC USE THEREOF

This application is a continuation of International application No. PCT/FR2006/001,782, filed Jul. 20, 2006, which is incorporated herein by reference in its entirety; which claims the benefit of priority of French Patent Application No. 05/07, 803, filed Jul. 22, 2005.

The invention relates to compounds derived from N-(heteroaryl)-1-heteroarylalkyl-1H-indole-2-carboxamides which show in vitro and in vivo antagonist activity on receptors of TRPV1 (or VR1) type.

A first subject of the invention concerns compounds corresponding to the general formula (I) below.

Another subject of the invention concerns processes for preparing compounds of general formula (I).

Another subject of the invention concerns the use of the compounds of general formula (I) especially in medicaments or in pharmaceutical compositions.

The compounds of the invention correspond to the general formula (I):

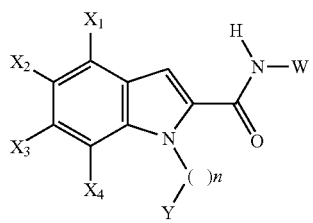

(I)

in which $X_1$, $X_2$, $X_3$ and $X_4$ represent, independently of each other, a hydrogen or halogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_1$-$C_6$-fluoroalkoxyl, cyano, C(O)$NR_1R_2$, nitro, $NR_1R_2$, $C_1$-$C_6$-thioalkyl, —S(O)—$C_1$-$C_6$-alkyl, —S(O)$_2$—$C_1$-$C_6$-alkyl, $SO_2NR_1R_2$, $NR_3COR_4$, $NR_3SO_2R_5$ or aryl group, the aryl being optionally substituted with one or more substituents chosen from a halogen and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_1$-$C_6$-fluoroalkoxyl, nitro or cyano group;

W represents a fused bicyclic group of formula:

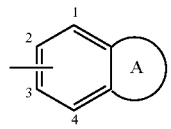

bonded to the nitrogen atom via positions 1, 2, 3 or 4;

A represents a 5- to 7-membered heterocycle comprising from one to three heteroatoms chosen from O, S and N;
the carbon atom(s) of A being optionally substituted with one or more groups chosen from a hydrogen atom and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl, aryl-$C_1$-$C_6$-alkylene, oxo or thio group;

the nitrogen atom(s) of A being optionally substituted with $R_6$ when the nitrogen is adjacent to a carbon atom substituted with an oxo group, or with $R_7$ in the other cases;

n is equal to 1, 2 or 3;

Y represents a heteroaryl optionally substituted with one or more groups chosen from a halogen atom and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, hydroxyl, $C_1$-$C_6$-alkoxyl, $C_1$-$C_6$-fluoroalkoxyl, cyano, C(O)$NR_1R_2$, nitro, $NR_1R_2$, $C_1$-$C_6$-thioalkyl, SH, —S(O)—$C_1$-$C_6$-alkyl, —S(O)$_2$—$C_1$-$C_6$-alkyl, $SO_2NR_1R_2$, $NR_3COR_4$, $NR_3SO_2R_5$, aryl-$C_1$-$C_6$-alkylene or aryl group, the aryl and the aryl-$C_1$-$C_6$-alkylene being optionally substituted with one or more substituents chosen from a halogen and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_1$-$C_6$-fluoroalkoxyl, nitro or cyano group;

$R_1$ and $R_2$ represent, independently of each other, a hydrogen atom or a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene or aryl group; or $R_1$ and $R_2$ together form, with the nitrogen atom that bears them, an azetidinyl, pyrrolidinyl, piperidyl, azepinyl, morpholinyl, thiomorpholinyl, piperazinyl or homopiperazinyl group, this group being optionally substituted with a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene or aryl group;

$R_3$ and $R_4$ represent, independently of each other, a hydrogen atom or a $C_1$-$C_6$-alkyl, aryl-$C_1$-$C_6$-alkylene or aryl group;

$R_5$ represents a $C_1$-$C_6$-alkyl, aryl-$C_1$-$C_6$-alkylene or aryl group;

$R_6$ represents a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-$C_1$-$C_6$-alkylene or aryl group;

$R_7$ represents a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-$C_1$-$C_6$-alkylene, $C_1$-$C_6$-alkyl-C(O)—, $C_3$-$C_7$-cycloalkyl-$C_1$-$C_3$-alkylene-(CO)—, $C_1$-$C_6$-fluoroalkyl-C(O)—, $C_3$-$C_7$-cycloalkyl-C(O)—, aryl-C(O)—, aryl-$C_1$-$C_6$-alkylene-C(O)—, $C_1$-$C_6$-alkyl-S(O)$_2$—, $C_1$-$C_6$-fluoroalkyl-S(O)$_2$—, $C_3$-$C_7$-cycloalkyl-S(O)$_2$—, $C_3$-$C_7$-cycloalkyl-$C_1$-$C_3$-alkylene-S(O)$_2$—, or aryl-$C_1$-$C_6$-alkylene-S(O)$_2$— or aryl group.

In the compounds of general formula (I):
the sulfur atom(s) of the heterocycle A or of the heterocycle Y may be in oxidized form (S(O) or S(O)$_2$);
the nitrogen atom(s) of the heterocycle A or of the heterocycle Y may be in oxidized form (N-oxide).

In the context of the invention, examples of groups W that may be mentioned include indolyl, isoindolyl, indolinyl, isoindolinyl, benzofuryl, dihydrobenzofuryl, benzothiophenyl, dihydrobenzothiophenyl, benzoxazolyl, dihydrobenzoxazolinyl, isobenzofuryl, dihydroisobenzofuryl, benzimidazolyl, dihydrobenzimidazolyl, indazolyl, benzothiazolyl, isobenzothiazolyl, dihydroisobenzothiazolyl, benzotriazolyl, quinolyl, dihydroquinolyl, tetrahydroquinolyl, isoquinolyl, dihydroisoquinolyl, tetrahydroisoquinolyl, benzoxazinyl, dihydrobenzoxazinyl, benzothiazinyl, dihydrobenzothiazinyl, cinnolinyl, quinazolinyl, dihydroquinazolinyl, tetrahydroquinazolinyl, quinoxalinyl, dihydroquinoxalinyl, tetrahydroquinoxalinyl, phthalazinyl, dihydrophthalazinyl, tetrahydrophthalazinyl, tetrahydrobenz[b]azepinyl, tetrahydrobenz[c]azepinyl, tetrahydrobenz[d]azepinyl, tetrahydrobenzo[b][1,4]diazepinyl, tetrahydrobenzo[e][1,4]diazepinyl, tetrahydro-benzo[b][1,4]oxazepinyl or tetrahydrobenzo[b][1,4]thiazepinyl groups.

Among the compounds of general formula (I) that are subjects of the invention, a first subgroup of compounds consists of the compounds for which:

$X_1$, $X_2$, $X_3$ and $X_4$ represent, independently of each other, a hydrogen or halogen atom, for example a fluorine atom, or a $C_1$-$C_6$-alkyl group, for example a tert-butyl group, or a $C_1$-$C_6$-fluoroalkyl group, for example a trifluoromethyl group.

Among the compounds of general formula (I) that are subjects of the invention, a second subgroup of compounds consists of the compounds for which:

$X_1$, $X_2$, $X_3$ and $X_4$ represent, independently of each other, a hydrogen or halogen atom, for example a fluorine atom, or a $C_1$-$C_6$-alkyl group, for example a tert-butyl group, a $C_1$-$C_6$-fluoroalkyl group, for example a trifluoromethyl group, or a group $NR_1R_2$, $R_1$ and $R_2$ being as defined in the general formula (I), for example a dimethylamine group.

Among the compounds of general formula (I) that are subjects of the invention, a third subgroup of compounds consists of the compounds for which:

$X_2$ is other than a hydrogen atom.

Among the compounds of general formula (I) that are subjects of the invention, a fourth subgroup of compounds consists of the compounds for which:

W represents a fused bicyclic group of formula:

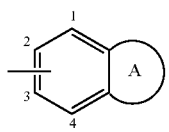

bonded to the nitrogen atom via positions 1, 2, 3 or 4;

and W is chosen from indolinyl, isoindolyl, isoindolinyl, benzofuryl, dihydrobenzofuryl, benzothiophenyl, dihydrobenzothiophenyl, benzoxazolyl, dihydrobenzoxazolinyl, isobenzofuryl, dihydroisobenzofuryl, benzimidazolyl, dihydrobenzimidazolyl, indolyl, indazolyl, benzothiazolyl, isobenzothiazolyl, dihydroisobenzothiazolyl, benzotriazolyl, quinolyl, dihydroquinolyl, tetrahydroquinolyl, isoquinolyl, dihydroisoquinolyl, tetrahydroisoquinolyl, benzoxazinyl, dihydrobenzoxazinyl, benzothiazinyl, dihydrobenzothiazinyl, cinnolinyl, quinazolinyl, dihydroquinazolinyl, tetrahydroquinazolinyl, quinoxalinyl, dihydroquinoxalinyl, tetrahydroquinoxalinyl, phthalazinyl, dihydrophthalazinyl, tetrahydrophthalazinyl, tetrahydrobenz[b]azepinyl, tetrahydrobenz[c]azepinyl, tetrahydrobenz[d]azepinyl, tetrahydrobenzo[b][1,4]diazepinyl, tetrahydrobenzo[e][1,4]diazepinyl, tetrahydrobenzo[b][1,4]oxazepinyl or tetrahydrobenzo[b][1,4]thiazepinyl groups;

the carbon and/or nitrogen atom(s) of the said group W being optionally substituted as defined in the general formula (I).

Among the compounds of the fourth subgroup, a fifth subgroup of compounds consists of the compounds for which:

W represents a fused bicyclic group of formula:

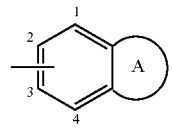

bonded to the nitrogen atom via positions 1, 2, 3 or 4;

and W is chosen from benzimidazolyl and indolyl groups; and/or the carbon atom(s) of A being optionally substituted with one or more $C_1$-$C_6$-alkyl groups, for example methyl; and/or the nitrogen atom(s) of A being optionally substituted with $R_7$, $R_7$ representing a $C_1$-$C_6$-alkyl group, for example methyl.

Among the compounds of the fifth subgroup, a sixth subgroup of compounds consists of the compounds for which:

W is chosen from benzimidazol-5-yl and indol-5-yl groups; and/or the carbon atom(s) of A being optionally substituted with one or more $C_1$-$C_6$-alkyl groups, for example a methyl; and/or the nitrogen atom(s) of A being optionally substituted with $R_7$, $R_7$ representing a $C_1$-$C_6$-alkyl group, for example a methyl.

Among the compounds of the fourth subgroup, a seventh subgroup of compounds consists of the compounds for which:

W represents a fused bicyclic group of formula:

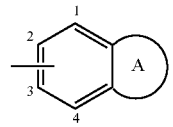

bonded to the nitrogen atom via positions 2 or 3;

and W is chosen from benzimidazolyl, indolyl, benzothiazolyl, quinolyl, tetrahydroquinolyl and benzoxazinyl groups; and/or the carbon atom(s) of A being optionally substituted with one or more $C_1$-$C_6$-alkyl groups, for example a methyl or an isopropyl, $C_1$-$C_6$-fluoroalkyl groups, for example a trifluoromethyl group, $C_3$-$C_7$-cycloalkyl groups, for example a cyclopropyl, or oxo groups; and/or the nitrogen atom(s) of A being optionally substituted with $R_6$ when the nitrogen is adjacent to a carbon atom substituted with an oxo group, $R_6$ representing a hydrogen atom or a $C_1$-$C_6$-alkyl group, for example a methyl; or with $R_7$ in the other cases, $R_7$ representing a $C_1$-$C_6$-alkyl group, for example a methyl, or a $C_3$-$C_7$-cycloalkyl-$C_1$-$C_3$-alkylene group, for example a cyclopropylmethyl.

Among the compounds of general formula (I) that are subjects of the invention, an eighth subgroup of compounds consists of the compounds for which:

n is equal to 1 or 2.

Among the compounds of general formula (I) that are subjects of the invention, a ninth subgroup of compounds consists of the compounds for which:

Y represents a heteroaryl, for example a pyridyl, an imidazolyl, a benzimidazolyl, a thiazolyl or a quinolyl, the heteroaryl being optionally substituted with one or more groups chosen from a $C_1$-$C_6$-alkyl group, for example a methyl, $NR_1R_2$ or aryl-$C_1$-$C_6$-alkylene, for example benzyl; $R_1$ and $R_2$ together forming, with the nitrogen atom that bears them, a morpholinyl group.

Among the compounds of general formula (I) that are subjects of the invention, a tenth subgroup of compounds consists of the compounds for which:

Y represents a heteroaryl chosen from pyridyl, pyrimidinyl, pyrazinyl, pyridazinyl, imidazolyl, benzimidazolyl, benzothiazolyl, thiazolyl, furyl, quinolyl, isoquinolyl and quinoxalinyl groups, the heteroaryl being optionally substituted with one or more groups chosen from a $C_1$-$C_6$-alkyl group, for example a methyl, a $C_1$-$C_6$-fluoroalkyl group, for example a trifluoromethyl group, an aryl-$C_1$-$C_6$-alkylene group, for example a benzyl, or $NR_1R_2$; $R_1$ and $R_2$ together forming, with the nitrogen atom that bears them, a morpholinyl group.

Among the compounds of general formula (I) that are subjects of the invention, an eleventh subgroup of compounds consists of the compounds for which:

W represents a benzimidazolyl group, the carbon and/or nitrogen atom(s) of the said group W being optionally substituted as defined in the general formula (I);

Y represents a pyridyl group optionally substituted as defined in the general formula (I).

Among the compounds of general formula (I) that are subjects of the invention, a twelfth subgroup of compounds consists of the compounds for which:

$X_1$, $X_2$, $X_3$ and $X_4$ represent, independently of each other, a hydrogen or halogen atom, for example a fluorine atom, or a $C_1$-$C_6$-alkyl group, for example a tert-butyl group, a $C_1$-$C_6$-fluoroalkyl group, for example a trifluoromethyl group, or $NR_1R_2$, $R_1$ and $R_2$ being as defined in the general formula (I), for example a dimethylamine group;
W represents a fused bicyclic group of formula:

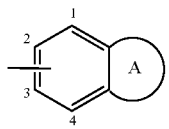

bonded to the nitrogen atom via positions 2 or 3; and W is chosen from benzimidazolyl, indolyl, benzothiazolyl, quinolyl, tetrahydroquinolyl and benzoxazinyl groups;
the carbon atom(s) of A being optionally substituted with one or more $C_1$-$C_6$-alkyl groups, for example methyl or isopropyl, $C_1$-$C_6$-fluoroalkyl groups, for example a trifluoromethyl group, $C_3$-$C_7$-cycloalkyl groups, for example cyclopropyl, or oxo groups; and/or
the nitrogen atom(s) of A being optionally substituted with $R_6$ when the nitrogen is adjacent to a carbon atom substituted with an oxo group, $R_6$ representing a hydrogen atom or a $C_1$-$C_6$-alkyl group, for example a methyl; or with $R_7$ in the other cases, $R_7$ representing a $C_1$-$C_6$-alkyl group, for example a methyl, or a $C_3$-$C_7$-cycloalkyl-$C_1$-$C_3$-alkylene group, for example a cyclopropylmethyl; and/or n is equal to 1 or 2; and/or
Y represents a heteroaryl, chosen from pyridyl, pyrimidinyl, pyrazinyl, pyridazinyl, imidazolyl, benzimidazolyl, benzothiazolyl, thiazolyl, furyl, quinolyl, isoquinolyl and quinoxalinyl groups, the heteroaryl being optionally substituted with one or more groups chosen from a $C_1$-$C_6$-alkyl group, for example a methyl, a $C_1$-$C_6$-fluoroalkyl group, for example a trifluoromethyl group, an aryl-$C_1$-$C_6$-alkylene group, for example a benzyl, or $NR_1R_2$; $R_1$ and $R_2$ together forming, with the nitrogen atom that bears them, a morpholinyl group.

Among the compounds of general formula (I) that are subjects of the invention, a thirteenth subgroup of compounds consists of the compounds for which:

$X_1$ and $X_4$ each represent a hydrogen atom;
$X_2$ and $X_3$ are such that one of the two represents a hydrogen atom whereas the other represents a group chosen from a halogen atom, for example a fluorine atom, or a $C_1$-$C_6$-alkyl group, for example a tert-butyl group, $C_1$-$C_6$-fluoroalkyl, for example a trifluoromethyl group, or $NR_1R_2$, $R_1$ and $R_2$ being as defined in the general formula (I), for example a dimethylamine group;
W represents a fused bicyclic group of formula:

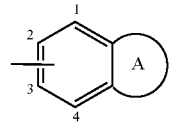

bonded to the nitrogen atom via positions 2 or 3; and W is chosen from benzimidazolyl, benzothiazolyl, quinolyl, tetrahydroquinolyl groups; the carbon atoms of A being optionally substituted with one or more $C_1$-$C_6$-alkyl groups, for example methyl; and/or
the nitrogen atom(s) of A being optionally substituted with $R_7$, $R_7$ representing a $C_1$-$C_6$-alkyl group, for example methyl;

n is equal to 1
Y represents a heteroaryl, for example a pyridyl, pyrazinyl, benzothiazolyl, quinolyl, isoquinolyl or quinoxalinyl group; the heteroaryl being optionally substituted with one or more $C_1$-$C_6$-alkyl groups, for example a methyl, or $NR_1R_2$; $R_1$ and $R_2$ together forming, with the nitrogen atom that bears them, a morpholinyl group.

The compounds for which $X_1$, $X_2$, $X_3$, $X_4$, W, n and Y are all as defined in the above subgroups of compounds form a fourteenth subgroup.

In the context of the present invention, the following meanings apply:

$C_t$-$C_z$ in which t and z may take the values from 1 to 7: a carbon-based chain possibly containing from t to z carbon atoms, for example $C_1$-$C_3$ is a carbon-based chain that may contain from 1 to 3 carbon atoms;

an alkyl: a saturated, linear or branched aliphatic group. Examples that may be mentioned include methyl, ethyl, propyl, isopropyl, butyl, isobutyl, tert-butyl, pentyl, etc. groups;

an alkylene: a saturated, linear or branched divalent alkyl group, for example a $C_{1-3}$-alkylene group represents a linear or branched divalent carbon-based chain of 1 to 3 carbon atoms, for example a methylene, ethylene, 1-methylethylene or propylene;

a cycloalkyl: a cyclic carbon-based group. Examples that may be mentioned include cyclopropyl, cyclobutyl, cyclopentyl, cyclohexyl, etc. groups;

a fluoroalkyl: an alkyl group of which one or more hydrogen atoms have been replaced with a fluorine atom;

an alkoxy: a radical —O-alkyl in which the alkyl group is as defined above;

a fluoroalkoxy: an alkoxy group of which one or more hydrogen atoms have been replaced with a fluorine atom;

a thioalkyl: a radical —S-alkyl in which the alkyl group is as defined above;

an aryl: a cyclic aromatic group containing between 6 and 10 carbon atoms.

Examples of aryl groups that may be mentioned include phenyl and naphthyl groups;

a heteroaryl: a 5- to 10-membered aromatic cyclic group containing from 1 to 4 heteroatoms chosen from O, S and N. Examples that may be mentioned include imidazolyl, thiazolyl, oxazolyl, furyl, thiophenyl, oxadiazolyl, tetrazolyl, pyridyl, pyrazinyl, pyrimidinyl, pyridazinyl, indolyl, benzofuryl, benzothiophenyl, benzoxazolyl, benzimidazolyl, indazolyl, benzothiazolyl, isobenzothiazolyl, benzotriazolyl, quinolyl, isoquinolyl and quinoxalinyl groups;

a heterocycle: a saturated, partially unsaturated or aromatic 5- to 7-membered cyclic group comprising from one to three heteroatoms chosen from O, S and N;

a halogen atom: a fluorine, a chlorine, a bromine or an iodine;

"oxo" means "=O";

"thio" means "=S".

The compounds of formula (I) may comprise one or more asymmetric carbon atoms. They may thus exist in the form of enantiomers or diastereoisomers. These enantiomers and diastereoisomers, and also mixtures thereof, including racemic mixtures, form part of the invention.

The compounds of formula (I) may exist in the form of bases or of acid-addition salts. Such addition salts form part of the invention.

These salts are advantageously prepared with pharmaceutically acceptable acids, but the salts of other acids that are useful, for example, for purifying or isolating the compounds of formula (I) also form part of the invention.

The compounds of general formula (I) may be in the form of hydrates or solvates, i.e. in the form of associations or combinations with one or more water molecules or with a solvent. Such hydrates and solvates also form part of the invention.

In the text hereinbelow, the term "leaving group" means a group that can be readily cleaved from a molecule by breaking a heterolytic bond, with loss of an electron pair. This group may thus be readily replaced with another group, for example during a substitution reaction. Such leaving groups are, for example, halogens or an activated hydroxyl group such as a methanesulfonate, benzenesulfonate, p-toluenesulfonate, triflate, acetate, etc. Examples of leaving groups and references for preparing them are given in "Advances in Organic Chemistry", J. March, 5$^{th}$ Edition, Wiley Interscience, 2001.

In accordance with the invention, the compounds of general formula (I) may be prepared according to the process illustrated in scheme 1 below.

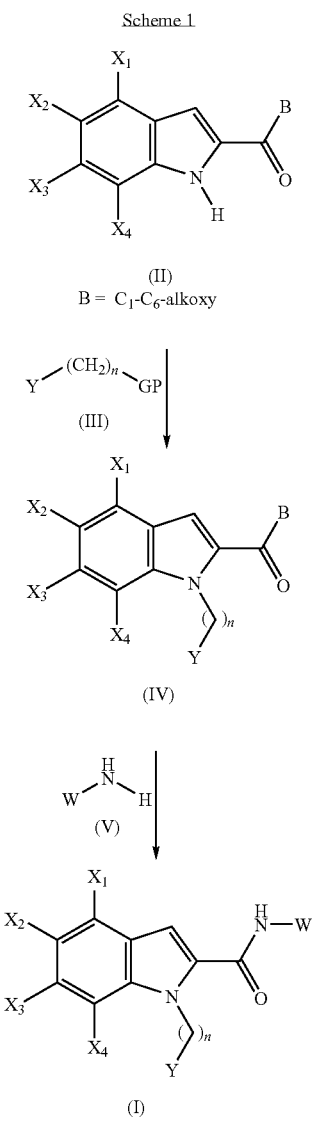

According to scheme 1, the compounds of general formula (IV) may be obtained by reacting a compound of general formula (II) in which $X_1$, $X_2$, $X_3$ and $X_4$ are as defined in the general formula (I) and B represents a $C_1$-$C_6$-alkoxy group, with a compound of general formula (III), in which Y and n are as defined in the general formula (I) and GP represents a leaving group or a hydroxyl group.

The compounds of general formula (II) are commercially available or prepared according to numerous processes described in the literature (for example D. Knittel *Synthesis* 1985, 2, 186; T. M. Williams *J. Med. Chem.* 1993, 36 (9), 1291; JP 2001151771 A2).

When the compound of general formula (III) is defined such that n is equal to 1, 2 or 3 and GP represents a leaving group such as a chlorine, bromine or iodine atom, the reaction may be performed in the presence of a base such as sodium hydride or potassium carbonate, in a polar solvent such as dimethylformamide, dimethyl sulfoxide or acetone (n=1:

Kolasa T., *Bioorg. Med. Chem.* 1997, 5 (3) 507, n=2: Abramovitch R., *Synth. Commun.*, 1995, 25(1), 1).

When the compound of general formula (III) is defined such that n is equal to 1, 2 or 3 and GP represents a hydroxyl group, the compounds of general formula (IV) may be obtained by reacting the compound of general formula (II) with a compound of general formula (III) in the presence of a phosphine, for instance triphenylphosphine and a reagent such as diethyl azodicarboxylate in solution in a solvent such as dichloromethane or tetrahydrofuran (O. Mitsunobu, *Synthesis*, 1981, 1-28).

The compound of general formula (I) is then obtained by reacting a compound of general formula (IV), as obtained above, with an amide of the compound of general formula (V), in which W is as defined in the general formula (I), in a refluxing solvent such as toluene. The amide of the compound of general formula (V) is prepared via the prior action of trimethylaluminum on the amines of general formula (V).

The compounds of general formulae (I), (II) and (IV), in which $X_1$, $X_2$, $X_3$ and/or $X_4$ represent a cyano group or an aryl, may be obtained via a coupling reaction, catalyzed with a metal such as palladium, performed on the corresponding compounds of general formulae (I), (II) and (IV), in which $X_1$, $X_2$, $X_3$ and/or $X_4$ represents a leaving group, for example a bromine, according to methods described in the literature or known to those skilled in the art.

The compounds of general formulae (I), (II) and (IV), in which $X_1$, $X_2$, $X_3$ and/or $X_4$ represent a group $C(O)NR_1R_2$, may be obtained from the corresponding compounds of general formulae (I), (II) and (IV), in which $X_1$, $X_2$, $X_3$ and/or $X_4$ represent a cyano group, according to methods described in the literature or known to those skilled in the art.

The compounds of general formulae (I), (II) and (IV), in which $X_1$, $X_2$, $X_3$ and/or $X_4$ represent a group —S(O)-alkyl or —S(O)$_2$-alkyl, may be obtained by oxidation of the corresponding compounds of general formulae (I), (II) and (IV), in which $X_1$, $X_2$, $X_3$ and/or $X_4$ represents a $C_1$-$C_6$-thioalkyl group, according to methods described in the literature or known to those skilled in the art.

The compounds of general formulae (I), (II) and (IV), in which $X_1$, $X_2$, $X_3$ and/or $X_4$ represent a group $NR_1R_2$, $NR_3COR_4$ or $NR_3SO_2R_5$, may be obtained from the corresponding compounds of general formulae (I), (II) and (IV), in which $X_1$, $X_2$, $X_3$ and/or $X_4$ represents a nitro group, for example by reduction, followed by acylation or sulfonylation, according to methods described in the literature or known to those skilled in the art.

The compounds of general formulae (I), (II) and (IV), in which $X_1$, $X_2$, $X_3$ and/or $X_4$ represent a group $NR_1R_2$, $NR_3COR_4$ or $NR_3SO_2R_5$, may be obtained from the corresponding compounds of general formulae (I), (II) and (IV), in which $X_1$, $X_2$, $X_3$ and/or $X_4$ represent, for example, a bromine atom, via coupling reaction, respectively, with an amine, an amide or a sulfonamide in the presence of a base, a phosphine and a palladium-based catalyst, according to methods described in the literature or known to those skilled in the art.

The compounds of general formulae (I), (II) and (IV), in which $X_1$, $X_2$, $X_3$ and/or $X_4$ represent a group $SO_2NR_1R_2$, may be obtained via a method analogous to that described in *Pharmazie* 1990, 45, 346, or according to methods described in the literature or known to those skilled in the art.

The compounds of general formula (I) in which $R_7$ represents a hydrogen atom may be obtained from compounds of general formula (I) in which, for example, $R_7$ represents a phenylmethyl group, by hydrogenation in the presence of a palladium-based catalyst, or by any method described in the literature or known to those skilled in the art.

In the text hereinabove, the compounds of formula (III) are commercially available, described in the literature (Carling R. W. et al *J. Med. Chem.* 2004 (47), 1807-1822 or Russel M. G. N. et al. *J. Med. Chem.* 2005 (48), 1367-1383) or available by using methods known to those skilled in the art. The compounds (V) and the other reagents, when their mode of preparation is not described, are commercially available or described in the literature (for example WO 03/049 702 or WO 03/068 749).

According to another of its aspects, a subject of the invention is also compounds of formula ($IV_{1-35}$) or ($V_{1-6}$). These compounds are useful as intermediates for the synthesis of the compounds of formula (I) and, more generally, in the preparation of therapeutic compounds.

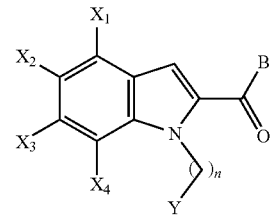

($IV_{1-35}$)

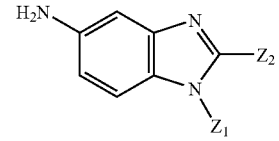

($V_{1-3}$)

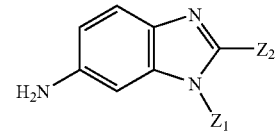

($V_{4-6}$)

The indoles ($IV_{1-35}$), listed in Table 1 were all prepared according to one of the methods described in Scheme 1.

Table 1 below illustrates the chemical structures and the physical properties of selected compounds of general formula ($IV_{1-35}$) according to the invention. In this table:

the "m.p." column gives the melting points of the products in degrees Celsius (° C.);

when the products were isolated in the form of an amorphous solid or an oil, they are characterized in this column by their mass ([MH]$^+$) or their NMR data (NMR) detailed below;

t-Bu represents a tert-butyl group, Me represents a methyl group and Et represents an ethyl group.

TABLE 1

(IV$_{1-35}$)

| No. | X$_1$, X$_2$, X$_3$, X$_4$ | n | Y | B | m.p. (° C.) |
|---|---|---|---|---|---|
| IV$_1$ | H, F, H, H | 1 | thiazol-2-yl | OEt | 95-96 |
| IV$_2$ | H, F, H, H | 2 | pyrid-3-yl | OEt | 105-106 |
| IV$_3$ | H, F, H, H | 1 | pyrid-3-yl | OEt | 104-105 |
| IV$_4$ | H, F, H, H | 1 | pyrid-4-yl | OEt | RMN |
| IV$_5$ | H, F, H, H | 1 | pyrid-2-yl | OEt | 67-69 |
| IV$_6$ | H, F, H, H | 1 | 2-methylpyrid-3-yl | OEt | [MH]$^+$ = 313 |
| IV$_7$ | H, F, H, H | 1 | 1-N-benzylimidazol-2-yl | OEt | 84-85 |
| IV$_8$ | H, F, H, H | 1 | 2-pyrrolidinopyrid-3-yl | OEt | [MH]$^+$ = 368 |
| IV$_9$ | H, F, H, H | 1 | 2-benzothiazol-2-yl | OEt | [MH]$^+$ = 355 |
| IV$_{10}$ | H, F, H, H | 1 | 1-methylbenzimidazol-2-yl | OEt | 198-199 |
| IV$_{11}$ | H, F, H, H | 2 | 4-methylthiazol-5-yl | OEt | [MH]$^+$ = 333 |
| IV$_{12}$ | H, F, H, H | 1 | quinol-2-yl | OEt | 105-106 |
| IV$_{13}$ | H, F, H, H | 1 | quinoxalin-2-yl | OEt | [MH]$^+$ = 350 |
| IV$_{14}$ | H, F, H, H | 1 | pyrazin-2-yl | OEt | [MH]$^+$ = 300 |
| IV$_{15}$ | H, F, H, H | 1 | 3-methylpyrid-2-yl | OEt | [MH]$^+$ = 313 |
| IV$_{16}$ | H, F, H, H | 1 | isoquinol-1-yl | OEt | 125-126 |
| IV$_{17}$ | H, F, H, H | 1 | 4-methylpyrid-2-yl | OEt | [MH]$^+$ = 313 |
| IV$_{18}$ | H, F, H, H | 2 | 2-methylpyrid-4-yl | OEt | [MH]$^+$ = 327 |
| IV$_{19}$ | H, F, H, H | 1 | 2-methylpyrid-4-yl | OEt | 71-72 |
| IV$_{20}$ | H, F, H, H | 1 | 5-methylpyrid-2-yl | OEt | [MH]$^+$ = 313 |
| IV$_{21}$* | H, F, H, H | 1 | dimethylpyrazin-2-yl* | OEt | [MH]$^+$ = 328* |
| IV$_{22}$ | H, F, H, H | 1 | 6-methylpyrazin-2-yl | OEt | [MH]$^+$ = 314 |
| IV$_{23}$ | H, F, H, H | 1 | 6-methylpyridazin-3-yl | OEt | [MH]$^+$ = 314 |
| IV$_{24}$ | H, F, H, H | 1 | 6-methylpyrid-2-yl | OEt | NMR |
| IV$_{25}$ | H, F, H, H | 1 | 2-phenylpyrid-4-yl | OEt | NMR |
| IV$_{26}$ | H, H, tBu, H | 1 | pyrid-4-yl | OMe | NMR |
| IV$_{27}$ | H, CF$_3$, H, H | 1 | pyrid-4-yl | OEt | NMR |
| IV$_{28}$ | H, H, NMe$_2$, H | 1 | pyrid-4-yl | OEt | NMR |
| IV$_{29}$ | H, H, CF$_3$, H | 1 | pyrid-4-yl | OMe | NMR |
| IV$_{30}$ | H, tBu, H, H | 1 | pyrid-4-yl | OEt | NMR |
| IV$_{31}$ | H, tBu, H, H | 1 | pyrid-2-yl | OEt | NMR |
| IV$_{32}$ | H, tBu, H, H | 1 | pyrid-3-yl | OEt | NMR |
| IV$_{33}$ | H, tBu, H, H | 1 | 2-methylpyrid-3-yl | OEt | [MH]$^+$ = 351 |
| IV$_{34}$ | H, tBu, H, H | 1 | 6-methylpyrid-2-yl | OEt | [MH]$^+$ = 351 |
| IV$_{35}$ | H, F, H, H | 1 | pyrimid-4-yl | OEt | [MH]$^+$ = 300 |

*The product IV$_{21}$ was obtained in the form of a mixture of 3 isomers used, without further purification, in the rest of the synthesis of (I), described in Scheme 1, to give, after separation by chromatography, products 94, 95 and 96 (see experimental section).

The NMR data for selected compounds of Table 1 are presented below:

Compound IV$_4$: $^1$H NMR (CDCl$_3$), δ (ppm): 1.3 (t, 3H); 4.2 (q, 2H); 5.79 (s, 2H); 6.82 (d, 2H); 7.07 (m, 2H); 7.27 (m, 2H); 8.41 (d, 2H).

Compound IV$_{24}$: $^1$H NMR (CDCl$_3$), δ (ppm): 1.38 (t, 3H); 2.6 (s, 3H); 4.32 (q, 2H); 5.91 (s, 2H); 6.39 (d, 1H); 7.05 (m, 2H); 7.35 (m, 4H).

Compound IV$_{25}$: $^1$H NMR (CDCl$_3$), δ (ppm): 1.54 (t, 3H); 4.51 (q, 2H); 6.1 (s, 2H); 6.97 (m, 1H); 7.29 (txd, 1H); 7.41 (m, 1H); 7.6 (m, 6H); 8.06 (m, 2H); 7.5 (d, 1H).

Compound IV$_{26}$: $^1$H NMR (DMSO D$_6$), δ (ppm): 1.25 (s, 9H); 3.79 (s, 3H); 5.90 (s, 2H); 6.96 (dxd, 2H); 7.27 (dxd, 1H); 7.35 (s, 1H); 7.46 (s, 1H); 7.66 (d, 1H); 8.45 (dxd, 2H).

Compound IV$_{27}$: $^1$H NMR (DMSO D$_6$), δ (ppm): 1.27 (t, 3H); 4.29 (q, 2H); 5.95 (s, 2H); 6.93 (d, 2H); 7.58 (s, 1H); 7.61 (dxd, 1H); 7.80 (d, 1H); 8.22 (s, 1H); 8.45 (dxd, 2H).

Compound IV$_{28}$: $^1$H NMR (DMSO D$_6$), δ (ppm): 1.23 (t, 3H); 2.91 (s, 6H); 4.2 (q, 2H); 5.79 (s, 2H); 6.56 (s, 1H); 6.8 (dxd, 1H); 6.94 (dxd, 2H); 7.26 (s, 1H); 7.52 (d, 1H); 8.45 (dxd, 2H).

Compound IV$_{29}$: $^1$H NMR (DMSO D$_6$), δ (ppm): 3.82 (s, 3H); 6 (s, 2H); 6.9 (d, 2H); 7.46 (d, 1H); 7.54 (s, 1H); 7.99 (d, 1H); 8.08 (s, 1H); 8.45 (dxd, 2H).

Compound IV$_{30}$: $^1$H NMR (CDCl$_3$), δ (ppm): 1.41 (m, 12H); 4.35 (q, 2H); 5.81 (s, 2H); 6.97 (d, 2H); 7.21 (d, 1H); 7.45 (m, 2H); 7.74 (m, 1H); 8.54 (d, 2H).

Compound IV$_{31}$: $^1$H NMR (DMSO D$_6$), δ (ppm): 1.25 (t, 3H); 1.32 (s, 9H); 4.25 (q, 2H); 5.88 (s, 2H); 6.79 (d, 1H); 7.22 (m, 1H); 7.32 (s, 1H); 7.4 (m, 2H); 7.65 (m, 2H); 8.46 (m, 1H).

Compound IV$_{32}$: $^1$H NMR (DMSO D$_6$), δ (ppm): 1.28 (t, 3H); 1.32 (s, 9H); 4.29 (q, 2H); 5.85 (s, 2H); 7.27 (m, 1H); 7.35 (m, 2H); 7.48 (m, 2H); 7.65 (d, 1H); 8.36 (d, 1H); 8.41 (d, 1H).

The amines ($V_{1-6}$) may be prepared according to the synthetic route described in Scheme 2.

In this scheme, $Z_1$ and $Z_2$ each independently represent a $C_1$-$C_6$-alkyl, $C_3$-$C_7$-cycloalkyl or $C_3$-$C_7$-cycloalkyl-$C_1$-$C_3$-alkylene group.

The cyclization using 4-nitro-1,2-phenylenediamine (VI) and a reagent such as a carboxylic acid of formula $Z_2$-$CO_2H$ in which $Z_2$ represents a $C_1$-$C_6$-alkyl, $C_3$-$C_7$-cycloalkyl or $C_3$-$C_7$-cycloalkyl-$C_1$-$C_3$-alkylene group allows the formation of the benzimidazole (VII). This product may then be substituted with a group $Z_1$, by reaction with a compound of formula $Z_1$-GP, in which GP is defined as in Scheme 1 and $Z_1$ represents a $C_1$-$C_6$-alkyl, $C_3$-$C_7$-cycloalkyl or $C_3$-$C_7$-cycloalkyl-$C_1$-$C_3$-alkylene group, for example in the presence of a base such as sodium hydride in a solvent such as tetrahydrofuran. The resulting mixture of benzimidazoles (VIII) is then converted into amines ($V_{1-6}$) by reduction, for example by catalytic hydrogenation in the presence of a catalyst such as palladium-on-charcoal or according to any other method for reducing a nitro group to an amine, known to those skilled in the art.

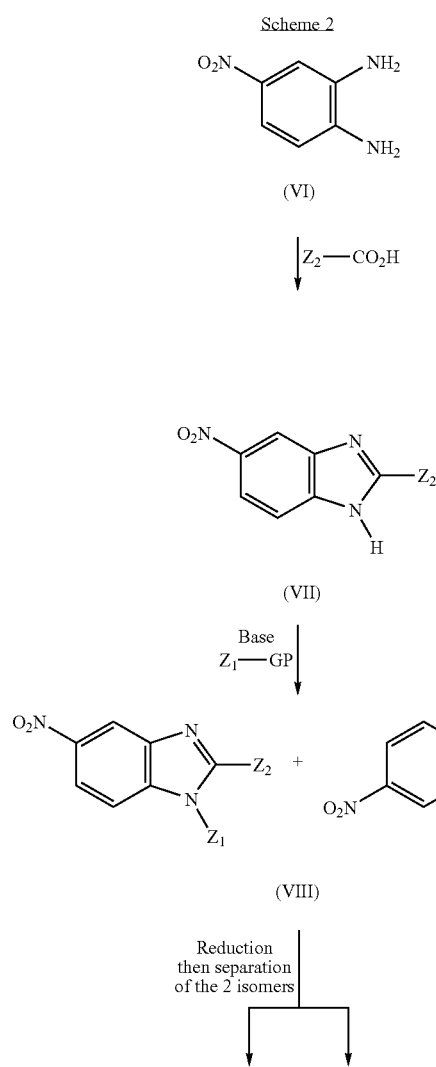

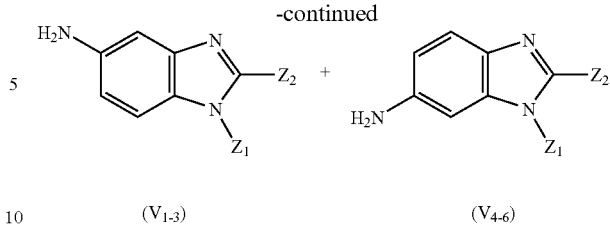

The amines ($V_{1-6}$) are listed in Tables 2a and 2b. The description of the mode of preparation of one of these amines is detailed in the experimental section.

TABLE 2a ($V_{1-3}$)

| No. | $Z_1$ | $Z_2$ | Mass $[MH]^+$ |
|---|---|---|---|
| $V_1$ | (cyclopropyl)methyl | methyl | 202 |
| $V_2$ | methyl | cyclopropyl | 188 |
| $V_3$ | methyl | isopropyl | 190 |

TABLE 2a ($V_{4-6}$)

| No. | $Z_1$ | $Z_2$ | Mass $[MH]^+$ |
|---|---|---|---|
| $V_4$ | (cyclopropyl)methyl | methyl | 202 |
| $V_5$ | methyl | cyclopropyl | 188 |
| $V_6$ | methyl | isopropyl | 190 |

The examples that follow describe the preparation of certain compounds in accordance with the invention. These examples are not limiting and serve merely to illustrate the present invention. The numbers of the compounds given as examples refer to those given in Table 3. The elemental microanalyses, LC-MS analyses (liquid chromatography coupled to mass spectrometry), IR spectra or NMR spectra confirm the structures of the compounds obtained.

EXAMPLE 1 (COMPOUND 3)

N-(1-Methyl-1H-indol-5-yl)-5-fluoro-1-[(pyrid-4-yl)methyl]-1H-indole-2-carboxamide hydrochloride (1:1)

1.1. Ethyl 5-fluoro-1-[(pyrid-4-yl)methyl]-1H-indole-2-carboxylate

A solution of 1 g (4.73 mmol) of ethyl 5-fluoro-1H-indole-2-carboxylate is added dropwise to a suspension of 0.38 g (9.45 mmol) of 60% sodium hydride in 10 ml of dimethylformamide, stirred at 0° C. under argon. The mixture is stirred for 30 minutes at 0° C. and then for 30 min at 20° C. The reaction mixture is cooled and 1.24 g (4.2 mmol) of 4-bromomethylpyridine hydrobromide are added portionwise. The mixture is stirred for 30 minutes at 0° C. and then for 30 minutes at 20° C. The reaction mixture is cooled again to 0° C. and a further 0.38 g (9.45 mmol) of 60% sodium hydride in 10 ml of dimethylformamide is added. After 30 minutes at 0° C., 1.24 g (4.2 mmol) of 4-bromomethylpyridine hydrobromide are added portionwise. The reaction mixture is then stirred for 20 hours at 20° C. After this time, the mixture is poured into a solution of 100 ml of ice-water and 100 ml of ethyl ether. The organic phase is separated out and the aqueous phase is re-extracted with 100 ml of ethyl ether. The organic phases are combined, washed with 50 ml of water and then dried over sodium sulfate, filtered and then concentrated under reduced pressure. The residue is purified by preparative chromatography (eluent: dichloromethane/acetone). 0.65 g of expected product is obtained in the form of an oil, which is used without further purification in the subsequent synthesis.

1.2 N-(1-Methyl-1H-indol-5-yl)-5-fluoro-1-[(pyrid-4-yl)methyl]-1H-indole-2-carboxamide hydrochloride (1:1) (Compound 3)

1.26 ml of trimethylaluminum (2M in toluene) are added under argon to a solution of 0.18 g (1.21 mmol) of 5-amino-1-methyl-1H-indole (I. T. Forbes, *J. Med. Chem.* 1993, 36 (8), 1104) in 10 ml of dry toluene. After 15 minutes, 0.3 g (1.01 mmol) of ethyl 5-fluoro-1-[(pyrid-4-yl)methyl]-1H-indole-2-carboxylate, obtained in step 1.1, is added. The reaction medium is refluxed for 4 hours and then stirred at room temperature overnight. It is poured onto ice and extracted with twice 30 ml of dichloromethane. The organic phases are combined, washed with 50 ml of water and then dried over sodium sulfate, filtered and then concentrated under reduced pressure. The residue is purified by preparative chromatography (eluent: dichloromethane/acetone). 0.35 g of a solid is obtained, which is dried under reduced pressure.

Melting point (base): 204-205° C.

The resulting solid is taken up in 30 ml of dichloromethane and 0.26 ml of a 4N solution of hydrogen chloride in dioxane is added. The solution is concentrated under reduced pressure and the resulting solid is recrystallized from a mixture of isopropanol and methanol. 0.33 g of the expected product is thus obtained in the form of a hydrochloride.

Melting point (1HCl): 258-260° C.

$^1$H NMR (DMSO $D_6$), δ (ppm): 3.76 (s, 3H); 6.1 (s, 2H); 6.33 (d, 1H); 7.11 (dxd, 1H); 7.25 (d, 2H); 7.37 (m, 2H); 7.52 (m, 5H); 7.9 (s, 1H); 8.7 (d, 2H).

EXAMPLE 2 (COMPOUND 4)

N-(1-Methyl-1H-benzimidazol-5-yl)-5-fluoro-1-[(pyrid-3-yl)methyl]-1H-indole-2-carboxamide hydrochloride (1:2)

2.1. Ethyl 5-fluoro-1-[(pyrid-3-yl)methyl]-1H-indole-2-carboxylate

A solution of 1 g (4.73 mmol) of ethyl 5-fluoro-1H-indole-2-carboxylate is added dropwise to a suspension of 0.38 g (9.45 mmol) of 60% sodium hydride in 10 ml of dimethylformamide, stirred at 0° C. under argon. The mixture is stirred for 30 minutes at 0° C. and then for 30 minutes at 20° C. The reaction mixture is cooled and 1.24 g (4.8 mmol) of 3-bromomethylpyridine hydrobromide are added portionwise. The mixture is stirred for 30 minutes at 0° C. and then for 30 minutes at 20° C. The reaction mixture is cooled again to 0° C. and a further 0.38 g (9.45 mmol) of 60% sodium hydride in 10 ml of dimethylformamide is added. After 30 minutes at 0° C., 1.24 g (4.8 mmol) of 3-bromomethylpyridine hydrobromide are added portionwise. The reaction mixture is stirred for 58 hours at 20° C. The mixture is then poured into a solution of 100 ml of ice-water and 100 ml of ethyl ether. The organic phase is separated out and the aqueous phase is re-extracted with 100 ml of ethyl ether. The organic phases are combined, washed with 50 ml of water and then dried over sodium sulfate, filtered and then concentrated under reduced pressure. The residue is purified by preparative chromatography (eluent: dichloromethane/acetone). 0.5 g of expected product is obtained in the form of a solid, which is used without further purification in the subsequent synthesis.

m.p.=104-105° C.

2.2 N-(1-Methyl-1H-benzimidazol-5-yl)-5-fluoro-1-[(pyrid-3-yl)methyl]-1H-indole-2-carboxamide hydrochloride (1:2) (Compound 4)

4.1 ml of trimethylaluminum (2M in toluene) are added under argon to a solution of 0.414 g (2.82 mmol) of 5-amino-1-methyl-1H-benzimidazole in 10 ml of dry toluene. After 15 minutes, 0.7 g (2.35 mmol) of ethyl 5-fluoro-1-[(pyrid-3-yl)methyl]-1H-indole-2-carboxylate, obtained in step 2.1, is added. The reaction medium is refluxed for 4 hours and then stirred overnight at room temperature. It is poured onto 100 g of ice and 50 ml of dichloromethane. A suspension is obtained, which is filtered and washed with water and ether. The residue is purified by preparative chromatography on alumina (eluent: dichloromethane/methanol). 0.36 g of a solid is obtained, which is dried under reduced pressure.

The resulting solid is taken up in 30 ml of dichloromethane and 0.55 ml of a 4N solution of hydrogen chloride in dioxane is added. The solution is concentrated under reduced pressure and the resulting solid is recrystallized from a mixture of isopropanol and methanol. 0.36 g of the expected product is thus obtained in the form of a hydrochloride.

Melting point (2HCl): 268-270° C.

$^1$H NMR (DMSO $D_6$), δ (ppm): 4.03 (s, 3H); 6 (s, 2H); 7.18 (dxd, 1H); 7.56 (dxd, 1H); 7.68 (m, 2H); 7.9 (m, 4H); 8.41 (s, 1H); 8.69 (m, 2H); 9.59 (s, 1H).

EXAMPLE 3 (COMPOUND 6)

N-(1,2-Dimethyl-1H-benzimidazol-5-yl)-5-t-butyl-1-[(pyrid-4-yl)methyl]-1H-indole-2-carboxamide hydrochloride (1:2)

3.1. Ethyl 5-t-butyl-1-[(pyrid-4-yl)methyl]-1H-indole-2-carboxylate

A solution of 1 g (4.08 mmol) of ethyl 5-t-butyl-1H-indole-2-carboxylate is added dropwise to a suspension of 0.33 g (8.15 mmol) of 60% sodium hydride in 10 ml of dimethylformamide, stirred at 0° C. under argon. The mixture is stirred for 30 minutes at 0° C. and then for 30 minutes at 20° C. The reaction mixture is cooled and 1.06 g (4.08 mmol) of 4-bromomethylpyridine hydrobromide are added portionwise. The mixture is stirred for 30 minutes at 0° C. and then for 30 minutes at 20° C. The reaction mixture is cooled again to 0° C. and a further 0.33 g (8.15 mmol) of 60% sodium hydride in 10 ml of dimethylformamide is added. After 30 minutes at 0° C., 1.06 g (4.08 mmol) of 4-bromomethylpyridine hydrobromide are added portionwise. The reaction mixture is then stirred for 20 hours at 20° C. After this time, the mixture is poured into a solution of 100 ml of ice-water and 70 ml of ethyl ether. The organic phase is separated out and the aqueous phase is re-extracted with 50 ml of ethyl ether. The organic phases are combined, washed with 50 ml of water and then dried over sodium sulfate, filtered and then concentrated under reduced pressure. The residue is purified by preparative chromatography (eluent: dichloromethane/acetone). 0.7 g of expected product is obtained in the form of an oil, which is used without further purification in the subsequent synthesis.

3.2 N-(1,2-Dimethyl-1H-benzimidazol-5-yl)-5-t-butyl-1-[(pyrid-4-yl)methyl]-1H-indole-2-carboxamide hydrochloride (1:2) (Compound 6)

0.9 ml of trimethylaluminum (2M in toluene) is added under argon to a solution of 0.24 g (1.43 mmol) of 5-amino-1,2-dimethyl-1H-benzimidazole (WO 2002059110) in 20 ml of dry toluene. After 15 minutes, 0.4 g (1.19 mmol) of ethyl 5-t-butyl-1-[(pyrid-4-yl)methyl]-1H-indole-2-carboxylate, obtained in step 3.1, is added. The reaction medium is refluxed for 4 hours and then stirred at room temperature overnight. It is poured onto 150 g of ice and 70 ml of dichloromethane. The aqueous phase is separated out and extracted with twice 30 ml of dichloromethane. The organic phases are combined, washed with 50 ml of water and then dried over sodium sulfate, filtered and then concentrated under reduced pressure. The residue is purified by preparative chromatography (eluent: dichloromethane/methanol). 0.4 g of a solid is obtained, which is dried under reduced pressure.

m.p. (base): 270-272° C.

The resulting solid is taken up in 30 ml of a 9/1 mixture of dichloromethane and methanol, and 0.5 ml of a 4N solution of hydrochloric acid in dioxane is added. The solution is concentrated under reduced pressure and the resulting solid is recrystallized from a mixture of ethanol and water. 0.22 g of the expected product is thus obtained in the form of a hydrochloride.

Melting point (2HCl): 295-300° C.

NMR $^1$H (DMSO D$_6$), δ (ppm): 1.31 (s, 9H), 2.79 (s, 3H), 3.89 (s, 3H); 6.08 (s, 2H); 7.42 (m, 4H); 7.8 (m, 4H); 8.3 (s, 1H); 8.7 (d, 2H); 10.9 (s, 1H exchangeable)

EXAMPLE 4 (COMPOUND 7)

N-(1,2-Dimethyl-1H-benzimidazol-5-yl)-5-fluoro-1-[(pyrid-4-yl)methyl]-1H-indole-2-carboxamide hydrochloride (1:2) (Compound 7)

1 ml of trimethylaluminum (2M in toluene) is added under argon to a solution of 0.27 g (1.61 mmol) of 5-amino-1,2-dimethyl-1H-benzimidazole (WO 02059110) in 20 ml of dry toluene. After 15 minutes, 0.4 g (1.34 mmol) of ethyl 5-fluoro-1-[(pyrid-4-yl)methyl]-1H-indole-2-carboxylate, obtained in the first step of Example 1, is added. The reaction medium is refluxed for 3 hours and then stirred at room temperature overnight. It is poured onto ice and extracted twice with 30 ml of dichloromethane. The organic phases are combined, washed with 50 ml of water and then dried over sodium sulfate, filtered and concentrated under reduced pressure. The residue is purified by preparative chromatography (eluent: dichloromethane/acetone). 0.46 g of a solid is obtained, which is dried under reduced pressure.

Melting point (base): 249-250° C.

The resulting solid is taken up in 30 ml of dichloromethane, and 0.26 ml of a 4N solution of hydrogen chloride in dioxane is added. The solution is concentrated under reduced pressure and the resulting solid is recrystallized from a mixture of isopropanol and methanol. 0.33 g of the expected product is thus obtained in the form of a hydrochloride.

Melting point (2HCl): 285-287° C.

$^1$H NMR (DMSO D$_6$), δ (ppm): 2.8 (s, 3H), 3.87 (s, 3H); 6.1 (s, 2H); 7.16 (dxd, 1H); 7.51 (m, 4H); 7.75 (s, 1H); 7.85 (d, 2H); 8.3 (s, 1H); 8.75 (d, 2H).

EXAMPLE 5 (COMPOUND 11)

N-(1-Methyl-1H-indol-5-yl)-5-fluoro-1-[(pyrid-3-yl)ethyl]-1H-indole-2-carboxamide 5.1. Ethyl 5-fluoro-1-[(pyrid-3-yl)ethyl]-1H-indole-2-carboxylate A solution of 0.365 g (1.44 mmol) of 1,1'-(azodicarbonyl)dipiperidine in 10 ml of tetrahydrofuran is added dropwise to a solution of 0.2 g (0.97 mmol) of ethyl 5-fluoro-1H-indole-2-carboxylate, 0.178 g (1.45 mmol) of 2-(pyrid-3-yl)ethanol and 0.36 ml (1.44 mmol) of tributylphosphine in 30 ml of tetrahydrofuran. The reaction mixture is stirred overnight at room temperature and then concentrated under reduced pressure and taken up in 50 ml of cyclohexane. The suspension is then filtered and the filtrate is chromatographed on a column of silica (eluent: dichloromethane/methanol). 0.125 g of the expected product is obtained.

5.2 N-(1-Methyl-1H-indol-5-yl)-5-fluoro-1-[(pyrid-3-yl)ethyl]-1H-indole-2-carboxamide (Compound 11)

0.54 ml of trimethylaluminum (2M in toluene) is added, at 0° C. under argon, to a solution of 0.7 g (0.478 mmol) of 5-amino-1-methyl-1H-indole (I. T. Forbes, *J. Med. Chem.* 1993, 36 (8), 1104) in 5 ml of dry toluene. After 15 minutes, 0.125 g (0.4 mmol) of ethyl 5-fluoro-1-[(pyrid-3-yl)ethyl]-1H-indole-2-carboxylate, obtained in step 5.1, is added. The reaction medium is refluxed for 5 hours and then stirred at room temperature overnight. It is poured onto 50 g of ice, 10 ml of 1N hydrochloric acid and 30 ml of ethyl acetate. The organic phase is separated out and 15 ml of 1N sodium hydroxide are added to the aqueous phase, which is re-extracted with a further 30 ml of ethyl acetate. The organic phases are combined, washed with saturated sodium chloride solution, dried over sodium sulfate and concentrated under reduced pressure. The residue obtained is taken up in 15 ml of isopropyl ether and the insoluble material is filtered off and then dried under reduced pressure. 50 mg of the expected product are thus isolated in the form of a solid.

Melting point (base): 188-189° C.

$^1$H NMR (CDCl$_3$), δ (ppm): 3.19 (t, 2H); 3.85 (s, 3H); 4.85 (t, 2H); 6.49 (d, 1H); 6.92 (s, 1H); 7.1 (m, 3H); 7.29 (m, 4H); 7.49 (dxt, 1H); 7.75 (m, 1H); 7.9 (s, 1H); 8.21 (d, 1H); 8.4 (d, 1H).

EXAMPLE 6 (COMPOUNDS 94, 95 AND 96)

N-(1,2-Dimethyl-1H-benzimidazol-5-yl)-5-fluoro-1-[(3,6-dimethylpyrazin-2-yl)methyl]-1H-indole-2-carboxamide (Compound 94)
N-(1,2-Dimethyl-1H-benzimidazol-5-yl)-5-fluoro-1-[(5,6-dimethylpyrazin-2-yl)methyl]-1H-indole-2-carboxamide (Compound 95)
N-(1,2-Dimethyl-1H-benzimidazol-5-yl)-5-fluoro-1-[(3,5-dimethylpyrazin-2-yl)methyl]-1H-indole-2-carboxamide (Compound 96)

6.1. (Chloromethyl)dimethylpyrazine (Mixture of 3 Isomers)

7.6 g (32.74 mmol) of trichloroisocyanuric acid are added, over 1 hour, to a solution, maintained at reflux, of 10 g of trimethylpyrazine (81.85 mmol) in 820 ml of dichloroethane. The reaction mixture is refluxed for 6 hours and then cooled to 20° C., stirred for a further 12 hours and filtered. The filtrate is concentrated under reduced pressure, taken up in 200 ml of ethyl ether, filtered again and then concentrated under reduced pressure. 9.6 g of methyldimethylpyrazine chloride are recovered in the form of a mixture, which is used without further purification in the following step.

6.2. Ethyl 5-fluoro-1-[(dimethylpyrazin-2-yl)methyl]-1H-indole-2-carboxylate (Mixture of Compounds IV$_{21}$)

A solution of 5 g (24.13 mmol) of ethyl 5-fluoro-1H-indole-2-carboxylate is added dropwise to a suspension of 1.45 g (36.2 mmol) of 60% sodium hydride in 200 ml of dimethylformamide, stirred at 0° C. under argon. The mixture is stirred for 30 minutes at 0° C. and then for 1 hour at 20° C. 9.45 g (60.33 mmol) of the mixture of methyldimethylpyrazine chloride obtained in the preceding step are then added portionwise. The mixture is stirred for 2 hours at 20° C., and 200 ml of water and 200 ml of ethyl acetate are then added. The organic phase is separated out and the aqueous phase is re-extracted with 100 ml of ethyl acetate. The organic phases are combined, washed with twice 50 ml of water, 50 ml of saturated aqueous sodium chloride solution and then dried over magnesium sulfate, filtered and concentrated under reduced pressure. The residue is purified by preparative chromatography (eluent: dichloromethane/ethyl acetate).

1.1 g of a mixture of the three expected isomers (IV$_{21}$) are obtained, which product is used without further purification in the subsequent synthesis.

6.3. N-(1,2-Dimethyl-1H-benzimidazol-5-yl)-5-fluoro-1-[(3,6-dimethylpyrazin-2-yl)methyl]-1H-indole-2-carboxamide (Compound 94)

N-(1,2-Dimethyl-1H-benzimidazol-5-yl)-5-fluoro-1-[(5,6-dimethylpyrazin-2-yl)methyl]-1H-indole-2-carboxamide (Compound 95)

N-(1,2-Dimethyl-1H-benzimidazol-5-yl)-5-fluoro-1-[(3,5-dimethylpyrazin-2-yl)methyl]-1H-indole-2-carboxamide (Compound 96)

2.57 ml of trimethylaluminum (2M in toluene) are added under argon to a solution of 0.568 g (3.53 mmol) of 5-amino-1,2-dimethyl-1H-benzimidazole (WO 02059110) in 20 ml of dry toluene. After 15 minutes, 1.05 g (3.21 mmol) of ethyl 5-fluoro-1-[(dimethylpyrazin-2-yl)methyl]-1H-indole-2-carboxylate, obtained in the preceding step, are added. The reaction medium is refluxed for 4 hours and then stirred at room temperature overnight. It is poured onto ice and extracted twice with 100 ml of ethyl acetate. The organic phases are combined, washed successively with 50 ml of water and 50 ml of saturated aqueous sodium chloride solution and then dried over magnesium sulfate, filtered and concentrated under reduced pressure. The residue is purified by preparative HPLC chromatography (eluents: ethanol/heptane/triethylamine).

The following are separated:

0.59 g of isomer 94 in the form of a solid,
Melting point: 269-275° C.
$^1$H NMR (DMSO D$_6$), δ (ppm): 2.31 (s, 3H); 2.46 (s, 3H); 2.6 (s, 3H); 3.69 (s, 3H); 5.95 (s, 2H); 7.02 (txd, 1); 7.4 (m, 5H); 7.86 (s, 1H); 8 (s, 1H)

0.139 g of isomer 95 in the form of a solid,
Melting point: 226-228° C.
$^1$H NMR (DMSO D$_6$), δ (ppm): 2.36 (s, 6H); 2.49 (s, 3H); 3.9 (s, 3H); 6.41 (s, 2H); 7.8 (txd, 1H); 8.06 (s, 1H); 8.2 (m, 1H); 8.29 (m, 2H); 8.4 (m, 1H); 8.71 (s, 2H); 11.6 (s, 1H)

and 0.51 g of isomer 96 in the form of a solid.
Melting point: 266-269° C.
$^1$H NMR (DMSO D$_6$), δ (ppm): 2.18 (s, 3H); 2.49 (s, 3H); 2.6 (s, 3H); 3.71 (s, 3H); 6.41 (s, 2H); 7.1 (txd, 1H); 7.4 (m, 5H); 7.85 (s, 1H); 8.2 (s, 1H); 10.3 (s, 1H).

EXAMPLE 7 (COMPOUND 32)

N-(1,2-Dimethyl-1H-benzimidazol-5-yl)-5-fluoro-1-[(pyrazin-2-yl)methyl]-1H-indole-2-carboxamide (Compound 32)

7.1. Ethyl 5-fluoro-1-[(pyrazin-2-yl)methyl]-1H-indole-2-carboxylate (Compound IV$_{14}$)

According to a method analogous to that described in Example 6.2, 1.55 g of ethyl 5-fluoro-1-[(pyrazin-2-yl)methyl]-1H-indole-2-carboxylate (Compound IV$_{14}$) are isolated starting with 2 g (9.65 mmol) of ethyl 5-fluoro-1H-indole-2-carboxylate [MH]$^+$=300

7.2. N-(1,2-Dimethyl-1H-benzimidazol-5-yl)-5-fluoro-1-[(pyrazin-2-yl)methyl]-1H-indole-2-carboxamide (Compound 32)

According to a method analogous to that described in Example 6.3, 0.2 g of N-(1,2-dimethyl-1H-benzimidazol-5-yl)-5-fluoro-1-[(pyrazin-2-yl)methyl]-1H-indole-2-carboxamide (Compound 32) is isolated, starting with 0.5 g of ethyl 5-fluoro-1-[(pyrazin-2-yl)methyl]-1H-indole-2-carboxylate (Compound IV$_{14}$).

Melting point: 239-240° C.
$^1$H NMR (DMSO D$_6$), δ (ppm): 2.5 (s, 3H); 3.7 (s, 3H); 5.98 (s, 2H); 7.11 (txd, 1H); 7.49 (m, 5H); 7.9 (d, 1H); 8.4 (s, 1H); 8.5 (s, 2H); 10.39 (s, 1H).

EXAMPLE 8 (COMPOUND 37)

N-(1,2-Dimethyl-1H-benzimidazol-5-yl)-5-fluoro-1-[(4-methylpyrid-2-yl)methyl]-1H-indole-2-carboxamide (Compound 37)

8.1. Ethyl 5-fluoro-1-[(4-methylpyrid-2-yl)methyl]-1H-indole-2-carboxylate (Compound IV$_{17}$)

According to a method analogous to that described in Example 6.2, 1.2 g of ethyl 5-fluoro-1-[(4-methylpyrid-2-yl)methyl]-1H-indole-2-carboxylate (Compound IV$_{17}$) are isolated, starting with 2 g (9.65 mmol) of ethyl 5-fluoro-1H-indole-2-carboxylate [MH]$^+$=313

8.2. N-(1,2-Dimethyl-1H-benzimidazol-5-yl)-5-fluoro-1-[(4-methylpyrid-2-yl)methyl]-1H-indole-2-carboxamide (Compound 37)

According to a method analogous to that described in Example 6.3, 0.48 g of N-(1,2-dimethyl-1H-benzimidazol-5-yl)-5-fluoro-1-[(4-methylpyrid-2-yl)methyl]-1H-indole-2-carboxamide (Compound 37) is isolated, starting with 0.51 g of ethyl 5-fluoro-1-[(4-methylpyrid-2-yl)methyl]-1H-indole-2-carboxylate (Compound $IV_{17}$)

Melting point: 213-215° C.

$^1$H NMR (DMSO $D_6$), δ (ppm): 2.18 (s, 3H); 2.49 (s, 3H); 3.67 (s, 3H); 5.88 (s, 2H); 6.82 (s, 1H); 7.08 (m, 2H); 7.4 (m, 5H); 7.9 (s, 1H); 8.39 (s, 1H); 10.4 (s, 1H).

EXAMPLE 9 (COMPOUND 67)

N-(1-Methyl-1H-indol-5-yl)-5-fluoro-1-[(pyrimid-4-yl)methyl]-1H-indole-2-carboxamide (Compound 67)

9.1. Ethyl 5-fluoro-1-[(pyrimid-4-yl)methyl]-1H-indole-2-carboxylate (Compound $IV_{35}$)

According to a method analogous to that described in Example 6.2, 2.6 g of ethyl 5-fluoro-1-[(pyrimid-4-yl)methyl]-1H-indole-2-carboxylate (Compound $IV_{35}$) are isolated, starting with 3.3 g (15.93 mmol) of ethyl 5-fluoro-1H-indole-2-carboxylate. $[MH]^+=300$

9.2. N-(1-methyl-1H-indol-5-yl)-5-fluoro-1-[(pyrimid-4-yl)methyl]-1H-indole-2-carboxamide (Compound 67)

According to a method analogous to that described in Example 6.3, 0.41 g of N-(1-methyl-1H-indol-5-yl)-5-fluoro-1-[(pyrimid-4-yl)methyl]-1H-indole-2-carboxamide (Compound 67) is isolated, starting with 0.5 g of ethyl 5-fluoro-1-[(pyrimid-4-yl)methyl]-1H-indole-2-carboxylate (Compound $IV_{35}$).

Melting point: 199-200° C.

$^1$H NMR (DMSO $D_6$), δ (ppm): 2.5 (s, 3H); 3.69 (s, 3H); 5.93 (s, 2H); 6.91 (d, 1H); 7.08 (txd, 1H); 7.42 (m, 5H); 7.85 (s, 1H); 8.62 (d, 1H); 9.03 (s, 1H); 10.31 (s, 1H).

EXAMPLE 10 (COMPOUND 68)

N-(1,2-Dimethyl-1H-benzimidazol-5-yl)-5-fluoro-1-[(6-methylpyrazin-2-yl)methyl]-1H-indole-2-carboxamide (Compound 68)

10.1. Ethyl 5-fluoro-1-[(6-methylpyrazin-2-yl)methyl]-1H-indole-2-carboxylate (Compound $IV_{22}$)

According to a method analogous to that described in Example 6.2, 0.32 g of ethyl 5-fluoro-1-[(6-methylpyrazin-2-yl)methyl]-1H-indole-2-carboxylate (Compound $IV_{22}$) is isolated, starting with 3.3 g (15.93 mmol) of ethyl 5-fluoro-1H-indole-2-carboxylate. $[MH]^+=314$

10.2. N-(1,2-Dimethyl-1H-benzimidazol-5-yl)-5-fluoro-1-[(6-methylpyrazin-2-yl)methyl]-1H-indole-2-carboxamide (Compound 68)

According to a method analogous to that described in Example 6.3, 0.28 g of N-(1,2-dimethyl-1H-benzimidazol-5-yl)-5-fluoro-1-[(6-methylpyrazin-2-yl)methyl]-1H-indole-2-carboxamide (Compound 68) is isolated, starting with 0.38 g of ethyl 5-fluoro-1-[(6-methylpyrazin-2-yl)methyl]-1H-indole-2-carboxylate (Compound $IV_{22}$).

Melting point: 244-249° C.

$^1$H NMR (DMSO $D_6$), δ (ppm): 2.39 (s, 3H); 2.49 (s, 3H); 3.69 (s, 3H); 5.91 (s, 2H); 7.08 (m, 1H); 7.42 (m, 5H); 7.9 (s, 1H); 7.99 (s, 1H); 8.36 (s, 1H).

EXAMPLE 11 (COMPOUND 24)

N-(1,2-Dimethyl-1H-benzimidazol-5-yl)-5-trifluoromethyl-1-[(pyrid-4-yl)methyl]-1H-indole-2-carboxamide (Compound 24)

11.1. Ethyl 5-trifluoromethyl-1-[(pyrid-4-yl)methyl]-1H-indole-2-carboxylate (Compound $IV_{27}$)

A solution of 1.47 g (5.83 mmol) of 1,1'-(azodicarbonyl)dipiperidine in 50 ml of toluene is added dropwise to a solution of 1 g (3.89 mmol) of ethyl 5-trifluoromethyl-1H-indole-2-carboxylate, 0.63 g (5.83 mmol) of 4-pyridylcarbinol and 1.46 ml (5.83 mmol) of tributylphosphine in 50 ml of toluene. The reaction mixture is stirred overnight at room temperature and then concentrated under reduced pressure and chromatographed on a column of silica (eluent: dichloromethane/methanol). 1.05 g of expected product are obtained.

$^1$H NMR (DMSO $D_6$), δ (ppm): 1.27 (t, 3H); 4.29 (q, 2H); 5.95 (s, 2H); 6.93 (d, 2H); 7.58 (s, 1H); 7.61 (dxd, 1H); 7.80 (d, 1H); 8.22 (s, 1H); 8.45 (dxd, 2H).

11.2. N-(1,2-Dimethyl-1H-benzimidazol-5-yl)-5-trifluoromethyl-1-[(pyrid-4-yl)methyl]-1H-indole-2-carboxamide (Compound 24)

According to a method analogous to that described in Example 6.3, 0.65 g of N-(1,2-dimethyl-1H-benzimidazol-5-yl)-5-trifluoromethyl-1-[(pyrid-4-yl)methyl]-1H-indole-2-carboxamide (Compound 24) is isolated, starting with 0.5 g of ethyl 5-trifluoromethyl-1-[(pyrid-4-yl)methyl]-1H-indole-2-carboxylate (Compound $IV_{27}$).

Melting point: 250-251° C.

$^1$H NMR (DMSO $D_6$), δ (ppm): 2.49 (s, 3H); 3.69 (s, 3H); 5.95 (s, 2H); 6.98 (d, 1H); 7.49 (m, 4H); 7.69 (d, 1H); 7.9 (s, 1H); 7.99 (s, 1H); 8.19 (s, 1H); 8.42 (d, 2H).

EXAMPLE 12 (COMPOUND 91)

N-(2-Cyclopropyl-1-methyl-1H-benzimidazol-5-yl)-5-fluoro-1-[(pyrid-4-yl)methyl]-1H-indole-2-carboxamide (Compound 91)

12.1. 2-Cyclopropyl-5-nitro-1H-benzimidazole

By analogy with a described method (WO 96/04270), a solution of 5 g (32.65 mmol) of 4-nitro-1,2-phenylenediamine in 77 ml (0.979 mol) of cyclopropanecarboxylic acid is stirred at reflux for 14 hours. The reaction mixture is then concentrated under reduced pressure and taken up in 150 ml of ethyl acetate and 100 ml of sodium hydrogen carbonate. The organic phase is washed with 100 ml of water and then with 50 ml of saturated sodium chloride solution, dried over magnesium sulfate and then concentrated under reduced pressure. 6.5 g of a brown oil are obtained, and are used without further purification in the following step.

12.2. 2-Cyclopropyl-1-methyl-5-nitro-1H-benzimidazole and 2-cyclopropyl-1-methyl-6-nitro-1H-benzimidazole A solution of 6.5 g (32 mmol) of 2-cyclopropyl-5-nitro-1H-benzimidazole, obtained in the preceding step, in 20 ml of tetrahydrofuran is added dropwise to a stirred suspension, under argon at room temperature, of 2.6 g of sodium hydride (63.98 mmol) in 150 ml of tetrahydrofuran. The reaction mixture is stirred for 3 hours at 20° C. and 2.2 ml (35.2 mmol) of methyl iodide are then added. Stirring is continued for a further 48 hours. The reaction mixture is then concentrated under reduced pressure and then chromatographed directly on a column of silica (eluent: dichloromethane/methanol). 4.5 g of the expected mixture of isomers are thus obtained in the form of a solid, which is used without further purification in the following step.

12.3. 2-Cyclopropyl-1-methyl-5-amino-1H-benzimidazole (Compound $V_2$) and 2-cyclopropyl-1-methyl-6-amino-1H-benzimidazole (Compound $V_5$)

15 g of ammonium formate (0.236 mol) are added to a suspension, stirred at 20° C., of 0.3 g of 10% palladium-on-charcoal in 50 ml of ethanol. This first reactor is connected to a second reactor in which is vigorously stirred at 20° C. a suspension of 4.5 g (20.7 mmol) of the mixture of 2-cyclopropyl-1-methyl-5-nitro-1H-benzimidazole and 2-cyclopropyl-1-methyl-6-nitro-1H-benzimidazole obtained in the preceding step and 0.4 g of 10% palladium-on-charcoal in 130 ml of ethanol.

After stirring for 48 hours at 20° C., 15 g (0.236 mol) of ammonium formate, 0.3 g of 10% palladium-on-charcoal and 50 ml of ethanol are added to the mixture, which is stirred for a further 24 hours and then filtered through a plug of Celite and concentrated under reduced pressure to give 4 g of an oil, which is purified by HPLC.

The following are separated:
1.1 g of product $V_2$,
[MH]$^+$=188
$^1$H NMR (DMSO D$_6$), δ (ppm): 1.05 (m, 4H); 2.25 (m, 1H); 3.81 (s, 3H); 6.61 (dxd, 1H); 6.72 (s, 1H); 7.26 (d, 1H)

0.92 g of product $V_5$
[MH]$^+$=188
$^1$H NMR (DMSO D$_6$), δ (ppm): 1.02 (m, 4H); 2.2 (m, 1H); 3.71 (s, 3H); 6.5 (dxd, 1H); 6.61 (s, 1H); 7.19 (d, 1H).

12.4. N-(2-Cyclopropyl-1-methyl-1H-benzimidazol-5-yl)-5-fluoro-1-[(pyrid-4-yl)methyl]-1H-indole-2-carboxamide (Compound 91)

1.26 ml of a 2N solution of trimethylaluminum in toluene are added dropwise to a solution of 0.376 g (2.01 mmol) of 2-cyclopropyl-1-methyl-5-amino-1H-benzimidazole ($V_2$) in 70 ml of toluene stirred at 0° C. under argon. The mixture is then maintained at 50° C. for 15 minutes and then cooled, and 0.5 g (1.68 mmol) of ethyl 5-fluoro-1-[(pyrid-4-yl)methyl]-1H-indole-2-carboxylate obtained in step 1.1 is then added portionwise. The mixture is stirred at reflux for 14 hours and then cooled. 15 ml of water and then 25 ml of 1N hydrochloric acid solution are added. The pH of the resulting solution is brought to pH>8 by addition of concentrated sodium hydroxide. A solid is filtered off, and taken up in 200 ml of ethyl acetate and 100 ml of water. The organic phase is separated out, dried over magnesium sulfate, concentrated under reduced pressure and then chromatographed (eluents: dichloromethane/methanol) to give 0.3 g of the expected product 91.
m.p.=260-261° C.
$^1$H NMR (DMSO D$_6$), δ (ppm): 1 (m, 4H); 2.19 (m, 1H); 3.82 (s, 3H); 5.9 (s, 2H); 7.02 (d, 2H); 7.12 (txd, 1H); 7.47 (m, 5H); 7.82 (d, 1H); 8.42 (d, 2H).

Table 3 below illustrates the chemical structures and the physical properties of selected compounds of general formula (I) according to the invention. In this table:
- the "m.p." column gives the melting points of the products in degrees Celsius (° C.);
- in the "salt/base" column, "-" represents a compound in free base form, whereas "HCl" represents a compound in hydrochloride form, and the ratio in parentheses is the (acid:base) ratio;
- t-Bu represents a tert-butyl group and Me represents a methyl group.

TABLE 3

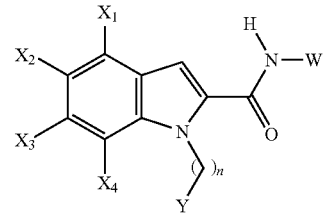

(I)

| N° | $X_1, X_2, X_3, X_4$ | n | Y | W | Salt/base | m.p. (° C.) |
|---|---|---|---|---|---|---|
| 1 | H, F, H, H | 1 | pyrid-4-yl | 1-methylbenzimidazol-5-yl | HCl (2:1) | 278-282 |
| 2 | H, F, H, H | 1 | pyrid-2-yl | 1-methylbenzimidazol-5-yl | HCl (2:1) | 255-260 |
| 3 | H, F, H, H | 1 | pyrid-4-yl | 1-methylindol-5-yl | HCl (1:1) | 258-260 |
| 4 | H, F, H, H | 1 | pyrid-3-yl | 1-methylbenzimidazol-5-yl | HCl (2:1) | 268-270 |
| 5 | H, F, H, H | 1 | pyrid-3-yl | 1-methylindol-5-yl | — | 214-215 |
| 6 | H, t-Bu, H, H | 1 | pyrid-4-yl | 1,2-dimethylbenzimidazol-5-yl | HCl (2:1) | 295-300 |
| 7 | H, F, H, H | 1 | pyrid-4-yl | 1,2-dimethylbenzimidazol-5-yl | HCl (2:1) | 285-287 |
| 8 | H, F, H, H | 1 | 2-methylpyrid-3-yl | 1-methylindol-5-yl | — | 249-250 |
| 9 | H, F, H, H | 1 | 6-methylpyrid-2-yl | 1-methylindol-5-yl | — | 205-206 |
| 10 | H, F, H, H | 1 | 2-morpholinylpyrid-3-yl | 1-methylindol-5-yl | — | 232-234 |

TABLE 3-continued

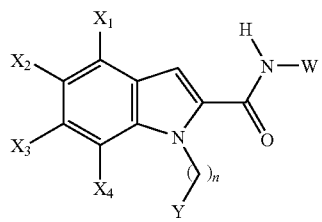

(I)

| N° | X₁, X₂, X₃, X₄ | n | Y | W | Salt/base | m.p. (° C.) |
|---|---|---|---|---|---|---|
| 11 | H, F, H, H | 2 | pyrid-3-yl | 1-methylindol-5-yl | — | 188-189 |
| 12 | H, F, H, H | 1 | 1-methylimidazol-2-yl | 1-methylindol-5-yl | — | 177-179 |
| 13 | H, F, H, H | 1 | pyrid-2-yl | 1-methylindol-5-yl | HCl (1:1) | 209-210 |
| 14 | H, F, H, H | 1 | 1-benzylimidazol-2-yl | 1-methylindol-5-yl | — | 243-244 |
| 15 | H, F, H, H | 2 | 4-methylthiazol-5-yl | 1-methylindol-5-yl | — | 205-206 |
| 16 | H, F, H, H | 1 | 1-methylbenzimid-azol-2-yl | 1-methylindol-5-yl | — | 260-262 |
| 17 | H, F, H, H | 1 | quinol-2-yl | 1-methylindol-5-yl | — | 266-267 |
| 18 | H, F, H, H | 1 | pyrid-4-yl | indol-5-yl | — | 298-300 |
| 19 | H, H, CF₃, H | 1 | pyrid-4-yl | 1,2-dimethylbenzimidazol-5-yl | — | 154-155 |
| 20 | H, F, H, H | 1 | quinol-2-yl | 1,2-dimethylbenzimidazol-5-yl | — HCl (1:1) | 254-255 292-296 |
| 21 | H, F, H, H | 1 | 5-trifluoromethyl-2-furyl | 1-methyl-1,2,3,4-tetrahydroquinol-7-yl | — | 237-238 |
| 22 | H, F, H, H | 1 | thiazol-2-yl | 1-methylindol-5-yl | — | 236-238 |
| 23 | H, F, H, H | 1 | pyrid-4-yl | 2-methylbenzimidazol-5-yl | — | 300-305 |
| 24 | H, CF₃, H, H | 1 | pyrid-4-yl | 1,2-dimethylbenzimidazol-5-yl | — | 250-251 |
| 25 | H, H, tBu, H | 1 | pyrid-4-yl | 1,2-dimethylbenzimidazol-5-yl | — | 229-230 |
| 26 | H, F, H, H | 1 | benzothiazol-2-yl | 1-methylindol-5-yl | — | 250-254 |
| 27 | H, F, H, H | 1 | benzothiazol-2-yl | 1,2-dimethylbenzimidazol-5-yl | — | 270-271 |
| 28 | H, F, H, H | 1 | quinoxalin-2-yl | 1-methylindol-5-yl | — | 212-214 |
| 29 | H, F, H, H | 2 | 2-methylpyrid-4-yl | 1,2-dimethylbenzimidazol-5-yl | — | 249-250 |
| 30 | H, F, H, H | 1 | isoquinol-1-yl | 1,2-dimethylbenzimidazol-5-yl | — | 263-268 |
| 31 | H, F, H, H | 1 | pyrazin-2-yl | 1-methylindol-5-yl | — | 197-207 |
| 32 | H, F, H, H | 1 | pyrazin-2-yl | 1,2-dimethylbenzimidazol-5-yl | — | 239-240 |
| 33 | H, F, H, H | 1 | pyrid-4-yl | 2-methylindol-5-yl | — | 260-261 |
| 34 | H, F, H, H | 1 | 4-methylpyrid-2-yl | 1-methylindol-5-yl | — | 202-204 |
| 35 | H, F, H, H | 1 | quinoxalin-2-yl | 1,2-dimethylbenzimidazol-5-yl | — | 243-247 |
| 36 | H, F, H, H | 1 | pyrid-4-yl | benzimidazol-5-yl | — | 255-257 |
| 37 | H, F, H, H | 1 | 4-methylpyrid-2-yl | 1,2-dimethylbenzimidazol-5-yl | — | 213-215 |
| 38 | H, F, H, H | 1 | 2-methylpyrid-4-yl | 1,2-dimethylbenzimidazol-5-yl | — | 263-265 |
| 39 | H, H, NMe₂, H | 1 | pyrid-4-yl | 1,2-dimethylbenzimidazol-5-yl | — | 255-256 |
| 40 | H, F, H, H | 1 | pyrid-4-yl | 1-methyl-2-trifluoromethyl-benzimidazol-5-yl | — | 224-226 |
| 41 | H, F, H, H | 1 | 3-methylpyrid-2-yl | 1-methylindol-5-yl | — | 198-199 |
| 42 | H, CF₃, H, H | 1 | pyrid-4-yl | indol-5-yl | — | 225-226 |
| 43 | H, CF₃, H, H | 1 | pyrid-4-yl | 1-methylindol-5-yl | — | 385-386 |
| 44 | H, CF₃, H, H | 1 | pyrid-4-yl | 2-methylbenzimidazol-5-yl | — | 294-296 |
| 45 | H, CF₃, H, H | 1 | pyrid-4-yl | 2-methylbenzothiazol-5-yl | — | 233-234 |
| 46 | H, CF₃, H, H | 1 | pyrid-4-yl | quinol-7-yl | — | 395-397 |
| 47 | H, H, NMe₂, H | 1 | pyrid-4-yl | indol-5-yl | — | 277-278 |
| 48 | H, H, NMe₂, H | 1 | pyrid-4-yl | 1-methylindol-5-yl | — | 226-227 |
| 49 | H, H, NMe₂, H | 1 | pyrid-4-yl | 2-methylbenzimidazol-5-yl | — | [MH]⁺ 425 |
| 50 | H, H, NMe₂, H | 1 | pyrid-4-yl | 2-methylbenzothiazol-5-yl | — | 256-257 |
| 51 | H, H, NMe₂, H | 1 | pyrid-4-yl | quinol-7-yl | — | 266-267 |
| 52 | H, H, CF₃, H | 1 | pyrid-4-yl | indol-5-yl | — | 332-333 |
| 53 | H, H, CF₃, H | 1 | pyrid-4-yl | 1-methylindol-5-yl | — | 230-231 |
| 54 | H, H, CF₃, H | 1 | pyrid-4-yl | 2-methylbenzimidazol-5-yl | — | 154-155 |
| 55 | H, H, CF₃, H | 1 | pyrid-4-yl | 2-methylbenzothiazol-5-yl | — | 252-253 |
| 56 | H, H, CF₃, H | 1 | pyrid-4-yl | quinol-7-yl | — | 237-238 |
| 57 | H, H, tBu, H | 1 | pyrid-4-yl | indol-5-yl | — | 255-256 |
| 58 | H, H, tBu, H | 1 | pyrid-4-yl | 1-methylindol-5-yl | — | [MH]⁺ 437 |
| 59 | H, H, tBu, H | 1 | pyrid-4-yl | 2-methylbenzimidazol-5-yl | — | 272-274 |
| 60 | H, H, tBu, H | 1 | pyrid-4-yl | 2-methylbenzothiazol-5-yl | — | 204-208 |
| 61 | H, H, tBu, H | 1 | pyrid-4-yl | quinol-7-yl | — | 280-282 |
| 62 | H, F, H, H | 1 | 3-methylpyrid-2-yl | 1,2-dimethylbenzimidazol-5-yl | — | 223-227 |
| 63 | H, F, H, H | 1 | pyrid-4-yl | 2-isopropyl-1-methyl-benzimidazol-5-yl | — | 138-139 |
| 64 | H, F, H, H | 1 | 5-methylpyrid-2-yl | 1-methylindol-5-yl | — | 188-190 |
| 65 | H, F, H, H | 1 | 5-methylpyrid-2-yl | 1,2-dimethylbenzimidazol-5-yl | — | 222-223 |
| 66 | H, F, H, H | 1 | 6-methylpyridazin-3-yl | 1-methylindol-5-yl | — | 226-227 |
| 67 | H, F, H, H | 1 | pyrimidin-4-yl | 1-methylindol-5-yl | — | 199-200 |
| 68 | H, F, H, H | 1 | 6-methylpyrazin-2-yl | 1,2-dimethylbenzimidazol-5-yl | — | 244-249 |
| 69 | H, F, H, H | 2 | pyrid-3-yl | 1,2-dimethylbenzimidazol-5-yl | — | 234-235 |

TABLE 3-continued (I)

| N° | X$_1$, X$_2$, X$_3$, X$_4$ | n | Y | W | Salt/base | m.p. (° C.) |
|---|---|---|---|---|---|---|
| 70 | H, tBu, H, H | 1 | pyrid-2-yl | indol-5-yl | — | 188-190 |
| 71 | H, tBu, H, H | 1 | pyrid-2-yl | 1-methylindol-5-yl | — | 161-163 |
| 72 | H, tBu, H, H | 1 | pyrid-2-yl | 1-methylbenzimidazol-5-yl | — | 223-225 |
| 73 | H, tBu, H, H | 1 | pyrid-2-yl | 4-methyl-3-oxo-2H-benzo[1,4]oxazin-6-yl | — | 136-138 |
| 74 | H, tBu, H, H | 1 | pyrid-2-yl | 1,2-dimethylbenzimidazol-5-yl | — | 272-274 |
| 75 | H, tBu, H, H | 1 | pyrid-2-yl | 2-methylbenzimidazol-5-yl | — | 222-224 |
| 76 | H, tBu, H, H | 1 | pyrid-2-yl | 2-methylbenzothiazol-5-yl | — | 176-178 |
| 77 | H, tBu, H, H | 1 | pyrid-2-yl | quinol-7-yl | — | 232-234 |
| 78 | H, tBu, H, H | 1 | pyrid-2-yl | 1-methyl-1,2,3,4-tetrahydroquinol-7-yl | — | 123-125 |
| 79 | H, tBu, H, H | 1 | pyrid-2-yl | 3-oxo-2H-benzo[1,4]oxazin-6-yl | — | [MH]$^+$ 455 |
| 80 | H, tBu, H, H | 1 | pyrid-3-yl | indol-5-yl | — | [MH]$^+$ 423 |
| 81 | H, tBu, H, H | 1 | pyrid-3-yl | 1-methylindol-5-yl | — | 291-292 |
| 82 | H, tBu, H, H | 1 | pyrid-3-yl | 1-methylbenzimidazol-5-yl | — | 272-274 |
| 83 | H, tBu, H, H | 1 | pyrid-3-yl | 4-methyl-3-oxo-2H-benzo[1,4]oxazin-6-yl | — | 125-127 |
| 84 | H, tBu, H, H | 1 | pyrid-3-yl | 1,2-dimethylbenzimidazol-5-yl | — | 279-281 |
| 85 | H, tBu, H, H | 1 | pyrid-3-yl | 2-methylbenzimidazol-5-yl | — | 235-237 |
| 86 | H, tBu, H, H | 1 | pyrid-3-yl | 2-methylbenzothiazol-5-yl | — | 235-237 |
| 87 | H, tBu, H, H | 1 | pyrid-3-yl | quinol-7-yl | — | 242-244 |
| 88 | H, tBu, H, H | 1 | pyrid-3-yl | 1-methyl-1,2,3,4-tetrahydroquinol-7-yl | — | 99-101 |
| 89 | H, tBu, H, H | 1 | pyrid-3-yl | 3-oxo-2H-benzo[1,4]oxazin-6-yl | — | 153-155 |
| 90 | H, F, H, H | 1 | pyrid-4-yl | 1-cyclopropylmethyl-2-methyl-benzimidazol-6-yl | — | 282-284 |
| 91 | H, F, H, H | 1 | pyrid-4-yl | 2-cyclopropyl-1-methyl-benzimidazol-5-yl | — | 260-261 |
| 92 | H, F, H, H | 1 | 6-methylpyridazin-3-yl | 1,2-dimethylbenzimidazol-5-yl | — | 240-243 |
| 93 | H, F, H, H | 1 | pyrimidin-4-yl | 1,2-dimethylbenzimidazol-5-yl | — | 242-244 |
| 94 | H, F, H, H | 1 | 3,6-dimethylpyrazin-2-yl | 1,2-dimethylbenzimidazol-5-yl | — | 269-275 |
| 95 | H, F, H, H | 1 | 5,6-dimethylpyrazin-2-yl | 1,2-dimethylbenzimidazol-5-yl | — | 226-228 |
| 96 | H, F, H, H | 1 | 3,5-dimethylpyrazin-2-yl | 1,2-dimethylbenzimidazol-5-yl | — | 266-269 |
| 97 | H, F, H, H | 1 | pyrid-4-yl | 1-(cyclopropyl)methyl-2-methylbenzimidazol-5-yl | — | 232-233 |
| 98 | H, tBu, H, H | 1 | pyrid-4-yl | 3-oxo-2H-benzo[1,4]oxazin-6-yl | — | 276-278 |
| 99 | H, tBu, H, H | 1 | pyrid-4-yl | 1-methyl-1,2,3,4-tetrahydroquinol-7-yl | — | 292-293 |
| 100 | H, tBu, H, H | 1 | pyrid-4-yl | quinol-7-yl | — | 203-205 |
| 101 | H, tBu, H, H | 1 | pyrid-4-yl | indol-5-yl | — | 336-338 |
| 102 | H, tBu, H, H | 1 | pyrid-4-yl | 1-methylindol-5-yl | — | 248-250 |
| 103 | H, tBu, H, H | 1 | pyrid-4-yl | 1-methylbenzimidazol-5-yl | — | 259-261 |
| 104 | H, tBu, H, H | 1 | pyrid-4-yl | 4-methyl-3-oxo-2H-benzo[1,4]oxazin-6-yl | — | 218-220 |
| 105 | H, tBu, H, H | 1 | pyrid-4-yl | benzimidazol-5-yl | — | 292-293 |
| 106 | H, tBu, H, H | 1 | pyrid-4-yl | 2-methylbenzothiazol-5-yl | — | 255-257 |

The compounds of the invention were subjected to in vitro and in vivo pharmacological tests that demonstrated their value as substances with therapeutic activities.

The compounds of the invention also show solubility characteristics in water that favor good in vivo activity.

Test of inhibition of the current induced with capsaicin on rat DRGs

Primary Culture of Rat Dorsal Root Ganglion (DRG) Cells:

The neurons of the DRG naturally express the TRPV1 receptor.

The primary cultures of newborn rat DRGs are prepared using 1-day-old rats. Briefly, after dissection, the ganglions are trypsinized and the cells dissociated by mechanical trituration. The cells are resuspended in an Eagle basal culture medium containing 10% fetal calf serum, 25 mM KCl, 2 mM glutamine, 100 µg/ml gentamicin and 50 ng/ml of NGF, and then deposited on glass slides coated with laminin (0.25×10$^6$ cells per slide), which are then placed in Corning 12-well dishes. The cells are incubated at 37° C. in a humidified atmosphere containing 5% CO$_2$ and 95% air. Cytosine β-D-arabinoside (1 µM) is added 48 hours after culturing, to prevent the growth of non-neuronal cells. The slides are transferred into experimental chambers for the patch-clamp studies after 7-10 days of culturing.

Electrophysiology:

The measuring chambers (volume 800 μl) containing the cell preparation are placed on the platform of an inverted microscope (Olympus IMT2) equipped with Hoffman optics (Modulation Contrast, New York) and observed at a magnification of 400×. The chambers are continuously gravity-influxed (2.5 ml/min) using a solution distributor accepting 8 inlets and whose sole outlet, consisting of a polyethylene tube (aperture 500 μm), is placed less than 3 mm from the cell under study. The "whole cell" configuration of the patch-clamp technique was used. The borosilicate-glass pipettes (resistance 5-10 MOhms) are brought to the cell by means of a 3D piezoelectric micromanipulator (Burleigh, PC1000). The overall currents (membrane potential set at −60 mV) are recorded with an Axopatch 1D amplifier (Axon Instruments, Foster City, Calif.), connected to a PC running the Pclamp8 software (Axon Instrument). The current plots are recorded on paper and simultaneously digitized (sampling frequency 15 to 25 Hz) and acquired on the hard drive of the PC.

The application of a 300 nM capsaicin solution induces on the DRG cells (voltage set at −70 mV) an entering cationic current. In order to minimize the desensitization of the receptors, a minimum interval of 1 minute between two applications of capsaicin is observed. After a control period (stabilization of the capsaicin response alone), the test compounds are applied alone at a given concentration (concentration of 10 nM or 1 nM) for a time of 4 to 5 minutes, during which several capsaicin+compound tests are performed (to obtain the maximum inhibition). The results are expressed as a percentage of inhibition of the control capsaicin response.

The percentages of inhibition of the capsaicin response (300 nM) are between 20% and 100% for the most active compounds of the invention tested at concentrations of 10 nM to 0.1 nM (see the example in Table 4).

The compounds of the invention are thus effective in vitro antagonists of receptors of TRPV 1 type.

TABLE 4

| Compound No. | % inhibition as a DRG patch |
| --- | --- |
| 6 | 80% (3 nM) |

Test of Mouse Corneal Irritation

The irritant nature of capsaicin is readily assessed on the cornea since this organ is one of the organs most densely innervated with C fibres. In this context, from preliminary experiments, the application of a very small amount of capsaicin (2 μl at a concentration of 160 μM) to the surface of the cornea of an animal leads to a certain number of stereotypic behavioral traits associated with irritation, which are easy to detect. Among these, the following are noted: blinking of the eye, rubbing of the instilled eye with the ipsilateral front paw, rubbing of the face with both front paws, scratching of the ipsilateral face with the hind paw. The duration of this behavior does not exceed the 2 minutes of observation, and the animal then resumes its normal activity. This aspect is moreover also normal. The mouse is not recluse in a corner with raised hackles and does not develop any observable sign of suffering. It may be concluded that the duration of action of capsaicin at these doses is less than 2 minutes.

Summary of the Methodology:

The principle of the series of experiments is to determine whether the compounds of the invention can influence the behavioral response induced with a given amount of capsaicin. The capsaicin is initially diluted to 25 mM in DMSO and diluted, for its final use, in Tween 80 to 10% in physiological saline. It appears, from control studies, that, under these conditions, the solvent has no effect.

In practice, the test product is administered orally and, with a delay (pretreatment time: t) that depends on the pharmacokinetic data, the animal receives an ocular instillation of 2 μl of a 160 μM capsaicin solution prepared as indicated above. During a 2-minute observation following the instillation, the number of times the instilled eye is rubbed with the ipsilateral front paw is recorded.

For a given animal, the percentage of protection is calculated as follows:

$P=100-((\text{number of scratching actions observed/mean number of scratching actions for the group treated with the solvent})\times 100)$ This percentage of protection is averaged for each group of animals (n=number of animals tested with the compound of the invention).

The percentages of protection evaluated in this model for the most active compounds of the invention, used at a dose of 1 mg/kg (po), are between 20% and 100% (see the selected examples in Table 5):

TABLE 5

| Compound No. | % P - (t) at 1 mg/kg (po) |
| --- | --- |
| 6 | 24% - (1 h) |
| 3 | 44% - (1 h) |

The results of these tests show that the most active compounds of the invention block the effects induced by stimulation of the TRPV1 receptors.

The compounds of the invention may thus be used for the preparation of medicaments, especially for the preparation of a medicament for preventing or treating pathologies in which the TRPV1 receptors are involved.

Thus, according to another of its aspects, a subject of the invention is medicaments that comprise a compound of formula (I), or a pharmaceutically acceptable salt, or alternatively a hydrate or a solvate of the said compound.

These medicaments find therapeutic use especially in the prevention and/or treatment of pain and inflammation, chronic pain, neuropathic pain (trauma-related, diabetic, metabolic, infection-related or toxic pain, or pain induced by an anticancer or iatrogenic treatment), (osteo)arthritic pain, rheumatic pain, fibromyalgia, back pain, cancer-related pain, facial neuralgia, headaches, migraine, dental pain, burns, sunburn, animal bites or insect bites, post-herpetic neuralgia, muscular pain, trapped nerves (central and/or peripheral), spinal column and/or brain trauma, ischaemia (of the spinal column and/or the brain), neurodegeneration, hemorrhagic strokes (of the spinal column and/or of the brain) and post-stroke pain.

The compounds of the invention may be used for the preparation of a medicament for preventing and/or treating urological disorders such as hyperactivity of the bladder, vesical hyperreflexia, vesical instability, incontinence, urgent micturition, urinary incontinence, cystitis, nephritic colic, pelvic hypersensitivity and pelvic pain.

The compounds of the invention may be used to prepare a medicament for preventing and/or treating gynecological disorders, for instance vulvodynia and pain associated with salpingitis or with dysmenorrhea.

These products may also be used for the preparation of a medicament for preventing and/or treating gastrointestinal disorders such as gastroesophageal reflux disorder, stomach ulcers, duodenal ulcers, functional dyspepsia, colitis, IBS, Crohn's disease, pancreatitis, oesophagitis and biliary colic.

Similarly, the products of the present invention may be useful in the prevention and/or treatment of respiratory disorders such as asthma, coughing, COPD, bronchoconstriction and inflammatory disorders. These products may also be used for preventing and/or treating psoriasis, pruritus, dermal, ocular or mucous irritation, herpes and zona.

The compounds of the invention may also be used for the preparation of a medicament for treating depression.

The compounds of the invention may also be used for preparation of a medicament for treating diabetes.

According to another of its aspects, the present invention relates to pharmaceutical compositions comprising a compound according to the invention as active principle. These pharmaceutical compositions contain an effective dose of at least one compound according to the invention, or a pharmaceutically acceptable salt, a hydrate or solvate of the said compound, and also at least one pharmaceutically acceptable excipient.

The said excipients are chosen, according to the pharmaceutical form and the desired mode of administration, from the usual excipients known to those skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or the possible salt, solvate or hydrate thereof, may be administered in a unit administration form, as a mixture with standard pharmaceutical excipients, to man and animals for the prophylaxis or treatment of the disorders or diseases mentioned above.

The appropriate unit forms of administration include oral forms such as tablets, soft or hard gel capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms and implants. For topical application, the compounds according to the invention may be used in creams, gels, pomades or lotions.

By way of example, a unit form of administration of a compound according to the invention in tablet form may comprise the following components:

| | |
|---|---|
| Compound according to the invention | 50.0 mg |
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

The said unit forms are dosed to allow a daily administration of from 0.001 to 30 mg of active principle per kg of body weight, according to the galenical form.

There may be particular cases in which higher or lower dosages are appropriate: such dosages do not depart from the scope of the invention. According to the usual practice, the dosage that is appropriate for each patient is determined by the doctor according to the mode of administration, the weight and the response of the said patient.

According to another of its aspects, the present invention also relates to a method for treating the pathologies indicated above, which comprises the administration to a patient of an effective dose of a compound according to the invention, or a pharmaceutically acceptable salt, or hydrate or solvate thereof.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A compound of formula (I)

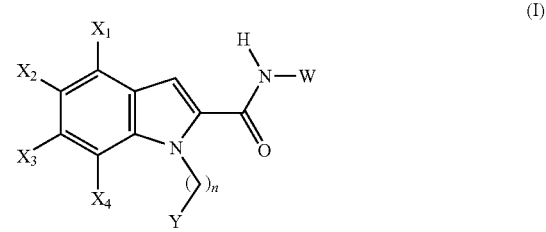

wherein:

$X_1$, $X_2$, $X_3$ and $X_4$ represent, independently of each other, a hydrogen or halogen atom, a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_1$-$C_6$-fluoroalkoxy, cyano, $C(O)NR_1R_2$, nitro, $NR_1R_2$, $C_1$-$C_6$-thioalkyl, —S(O)—$C_1$-$C_6$-alkyl, —S(O)$_2$—$C_1$-$C_6$-alkyl, $SO_2NR_1R_2$, $NR_3COR_4$, $NR_3SO_2R_5$ or aryl group, the aryl being optionally substituted with one or more substituents chosen from a halogen and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_1$-$C_6$-fluoroalkoxy, nitro or cyano group;

W represents a fused bicyclic group of formula:

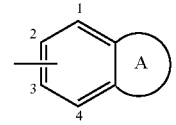

bonded to the nitrogen atom via positions 1, 2, 3 or 4; wherein

A represents a 5- to 7-membered heterocycle comprising from one to three heteroatoms chosen from O, S and N;

the carbon atom(s) of A being optionally substituted with one or more groups chosen from a hydrogen atom, a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl, aryl-$C_1$-$C_6$-alkylene, oxo or thio group;

the nitrogen atom(s) of A being optionally substituted with $R_6$ when the nitrogen is adjacent to a carbon atom substituted with an oxo group, or with $R_7$ in the other cases;

n is equal to 1, 2 or 3;

Y represents a heteroaryl optionally substituted with one or more groups chosen from a halogen atom and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, hydroxyl, $C_1$-$C_6$-alkoxy, $C_1$-$C_6$-fluoroalkoxy, cyano, $C(O)NR_1R_2$, nitro, $NR_1R_2$, $C_1$-$C_6$-thioalkyl, SH, —S(O)—$C_1$-$C_6$-alkyl, —S(O)$_2$—$C_1$-$C_6$-alkyl, SO$_2$NR$_1$R$_2$, NR$_3$COR$_4$, NR$_3$SO$_2$R$_5$, aryl-$C_1$-$C_6$-alkylene or aryl group, the aryl and the aryl-$C_1$-$C_6$-alkylene being optionally substituted with one or more substituents chosen from a halogen and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_1$-$C_6$-fluoroalkoxy, nitro or cyano group;

R$_1$ and R$_2$ represent, independently of each other, a hydrogen atom or a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene or aryl group; or R$_1$ and R$_2$ together form, with the nitrogen atom that bears them, an azetidinyl, pyrrolidinyl, piperidyl, azepinyl, morpholinyl, thiomorpholinyl, piperazinyl or homopiperazinyl group, this group being optionally substituted with a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene or aryl group;

R$_3$ and R$_4$ represent, independently of each other, a hydrogen atom or a $C_1$-$C_6$-alkyl, aryl-$C_1$-$C_6$-alkylene or aryl group;

R$_5$ represents a $C_1$-$C_6$-alkyl, aryl-$C_1$-$C_6$-alkylene or aryl group;

R$_6$ represents a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-$C_1$-$C_6$-alkylene or aryl group;

R$_7$ represents a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-$C_1$-$C_6$-alkylene, $C_1$-$C_6$-alkyl-C(O)—, $C_3$-$C_7$-cycloalkyl-$C_1$-$C_3$-alkylene-(CO)—, $C_1$-$C_6$-fluoroalkyl-C(O)—, $C_3$-$C_7$-cycloalkyl-C(O)—, aryl-C(O)—, aryl-$C_1$-$C_6$-alkylene-C(O)—, $C_1$-$C_6$-alkyl-S(O)$_2$—, $C_1$-$C_6$-fluoroalkyl-S(O)$_2$—, $C_3$-$C_7$-cycloalkyl-S(O)$_2$—, $C_3$-$C_7$-cycloalkyl-$C_1$-$C_3$-alkylene-S(O)$_2$—, aryl-S(O)$_2$—, aryl-$C_1$-$C_6$-alkylene-S(O)$_2$— or aryl group;

the sulfur atom(s) of the heterocycle A or of the heteroaryl Y optionally being in oxidized form;

the nitrogen atom(s) of the heterocycle A or of the heteroaryl Y optionally being in oxidized form;

or an acid-addition salt thereof.

2. The compound of formula (I) according to claim 1, wherein X$_1$, X$_2$, X$_3$, X$_4$ represent, independently of each other, a hydrogen or halogen atom, a $C_1$-$C_6$-alkyl, $C_1$-$C_6$-fluoroalkyl group or a group NR$_1$R$_2$, and wherein R$_1$ and R$_2$ being as defined in claim 1;

or an acid-addition salt thereof.

3. The compound of formula (I) according to claim 1, wherein

W represents a fused bicyclic group of formula:

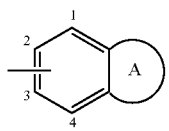

bonded to the nitrogen atom via positions 1, 2, 3 or 4;

and W is chosen from indolinyl, isoindolyl, isoindolinyl, benzofuryl, dihydrobenzofuryl, benzothiophenyl, dihydrobenzothiophenyl, benzoxazolyl, dihydrobenzoxazolinyl, isobenzofuryl, dihydroisobenzofuryl, benzimidazolyl, dihydrobenzimidazolyl, indolyl, indazolyl, benzothiazolyl, isobenzothiazolyl, dihydroisobenzothiazolyl, benzotriazolyl, quinolyl, dihydroquinolyl, tetrahydroquinolyl, isoquinolyl, dihydroisoquinolyl, tetrahydroisoquinolyl, benzoxazinyl, dihydrobenzoxazinyl, benzothiazinyl, dihydrobenzothiazinyl, cinnolinyl, quinazolinyl, dihydroquinazolinyl, tetrahydroquinazolinyl, quinoxalinyl, dihydroquinoxalinyl, tetrahydroquinoxalinyl, phthalazinyl, dihydrophthalazinyl, tetrahydrophthalazinyl, tetrahydrobenz[b]azepinyl, tetrahydrobenz[c]azepinyl, tetrahydrobenz[d]azepinyl, tetrahydrobenzo[b][1,4]diazepinyl, tetrahydrobenzo[e][1,4]diazepinyl, tetrahydrobenzo[b][1,4]oxazepinyl or tetrahydrobenzo[b][1,4]thiazepinyl groups; and wherein the carbon or nitrogen atom(s) of the said group W being optionally substituted one or more times with substituents as defined in claim 1;

or an acid-addition salt thereof.

4. The compound of formula (I) according to claim 1, wherein

W represents a fused bicyclic group of formula:

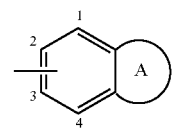

bonded to the nitrogen atom via positions 2 or 3;

and W is chosen from benzimidazolyl, indolyl, benzothiazolyl, quinolyl, tetrahydroquinolyl and benzoxazinyl groups; and wherein the carbon atom(s) of A being optionally substituted with one or more groups selected from $C_1$-$C_6$-alkyl, $C_1$-$C_6$-fluoroalkyl, $C_3$-$C_7$-cycloalkyl or oxo group; and the nitrogen atom(s) of A being optionally substituted with R$_6$ when the nitrogen is adjacent to a carbon atom substituted with an oxo group, R$_6$ representing a hydrogen atom or a $C_1$-$C_6$-alkyl group; or with R$_7$ in the other cases, wherein R$_7$ representing a $C_1$-$C_6$-alkyl group or a $C_3$-$C_7$-cycloalkyl-$C_1$-$C_3$-alkylene group;

or an acid-addition salt thereof.

5. The compound of formula (I) according to claim 1, wherein n is equal to 1 or 2;

or an acid-addition salt thereof.

6. The compound of formula (I) according to claim 1, wherein

Y represents a heteroaryl chosen from pyridyl, pyrimidinyl, pyrazinyl, pyridazinyl, imidazolyl, benzimidazolyl, benzothiazolyl, thiazolyl, furyl, quinolyl, isoquinolyl, quinoxalinyl groups, the heteroaryl being optionally substituted with one or more groups chosen from $C_1$-$C_6$-alkyl, $C_1$-$C_6$-fluoroalkyl, aryl-$C_1$-$C_6$-alkylene or NR$_1$R$_2$ groups; and wherein R$_1$ and R$_2$ together forming, with the nitrogen atom that bears them, a morpholinyl group;

or an acid-addition salt thereof.

7. The compound of formula (I) according to claim 1, wherein

X$_1$, X$_2$, X$_3$, X$_4$ represent, independently of each other, a hydrogen or halogen atom, a $C_1$-$C_6$-alkyl, $C_1$-$C_6$-fluoroalkyl or NR$_1$R$_2$ group, wherein R$_1$ and R$_2$ being as defined in claim 1:

W represents a fused bicyclic group of formula:

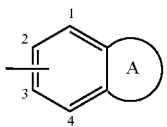

bonded to the nitrogen atom via positions 2 or 3; and W is chosen from benzimidazolyl, indolyl, benzothiazolyl, quinolyl, tetrahydroquinolyl or benzoxazinyl groups; and wherein the carbon atom(s) of A being optionally substituted with one or more $C_1$-$C_6$-alkyl, $C_1$-$C_6$-fluoroalkyl, $C_3$-$C_7$-cycloalkyl or oxo groups; and the nitrogen atom(s) of A being optionally substituted with $R_6$ when the nitrogen is adjacent to a carbon atom substituted with an oxo group, $R_6$ representing a hydrogen atom or a $C_1$-$C_6$-alkyl group; or with $R_7$ in the other cases, $R_7$ representing a $C_1$-$C_6$-alkyl group or a $C_3$-$C_7$-cycloalkyl-$C_1$-$C_3$-alkylene group;

n is equal to 1 or 2; and

Y represents a heteroaryl chosen from pyridyl, pyrimidinyl, pyrazinyl, pyridazinyl, imidazolyl, benzimidazolyl, benzothiazolyl, thiazolyl, furyl, quinolyl, isoquinolyl, quinoxalinyl groups, the heteroaryl being optionally substituted with one or more groups chosen from $C_1$-$C_6$-alkyl, $C_1$-$C_6$-fluoroalkyl, aryl-$C_1$-$C_6$-alkylene and $NR_1R_2$ groups; wherein $R_1$ and $R_2$ together forming, with the nitrogen atom that bears them, a morpholinyl group;

or an acid-addition salt thereof.

8. A process for preparing a compound of formula (I) according to claim 1, comprising:
reacting a compound of formula (IV)

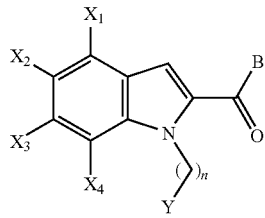

wherein $X_1$, $X_2$, $X_3$, $X_4$, Y and n are as defined in claim 1 and B represents a $C_1$-$C_6$-alkoxy group, with an amide of the compound of formula (V)

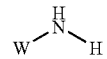

wherein W is as defined in claim 1, in a refluxing solvent, the amide of the compound of formula (V) being prepared via the prior action of trimethylaluminum on the amine of formula (V).

9. A pharmaceutical composition comprising a compound of formula (I) according to claim 1 or a pharmaceutically acceptable salt thereof in combination with at least one pharmaceutically acceptable excipient.

10. A pharmaceutical composition comprising a compound of formula (I) according to claim 2 or a pharmaceutically acceptable salt thereof in combination with at least one pharmaceutically acceptable excipient.

11. A pharmaceutical composition comprising a compound of formula (I) according to claim 3 or a pharmaceutically acceptable salt thereof in combination with at least one pharmaceutically acceptable excipient.

12. A pharmaceutical composition comprising a compound of formula (I) according to claim 4 or a pharmaceutically acceptable salt thereof in combination with at least one pharmaceutically acceptable excipient.

13. A pharmaceutical composition comprising a compound of formula (I) according to claim 5 or a pharmaceutically acceptable salt thereof in combination with at least one pharmaceutically acceptable excipient.

14. A pharmaceutical composition comprising a compound of formula (I) according to claim 6 or a pharmaceutically acceptable salt thereof in combination with at least one pharmaceutically acceptable excipient.

15. A pharmaceutical composition comprising a compound of formula (I) according to claim 7 or a pharmaceutically acceptable salt thereof in combination with at least one pharmaceutically acceptable excipient.

* * * * *

UNITED STATES PATENT AND TRADEMARK OFFICE
CERTIFICATE OF CORRECTION

| | | |
|---|---|---|
| PATENT NO. | : 7,745,467 B2 | Page 1 of 1 |
| APPLICATION NO. | : 11/970878 | |
| DATED | : June 29, 2010 | |
| INVENTOR(S) | : Laurent Dubois et al. | |

It is certified that error appears in the above-identified patent and that said Letters Patent is hereby corrected as shown below:

In column 10, line 7, delete "(Ill)" and insert -- (III) --, therefor.

In column 34, line 67, in claim 7, delete "1:" and insert -- 1; --, therefor.

Signed and Sealed this
First Day of February, 2011

David J. Kappos
*Director of the United States Patent and Trademark Office*